(12) United States Patent
Okell

(10) Patent No.: US 11,079,455 B2
(45) Date of Patent: Aug. 3, 2021

(54) COMBINED ANGIOGRAPHY AND PERFUSION USING RADIAL IMAGING AND ARTERIAL SPIN LABELING

(71) Applicant: Oxford University Innovation Limited, Oxford (GB)

(72) Inventor: Thomas Okell, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 315 days.

(21) Appl. No.: 15/731,113

(22) Filed: Apr. 20, 2017

(65) Prior Publication Data

US 2017/0307714 A1 Oct. 26, 2017

Related U.S. Application Data

(60) Provisional application No. 62/325,361, filed on Apr. 20, 2016.

(51) Int. Cl.

| G01R 33/563 | (2006.01) |
|---|---|
| A61B 5/055 | (2006.01) |
| A61B 5/026 | (2006.01) |
| A61B 5/00 | (2006.01) |
| G01R 33/48 | (2006.01) |

(52) U.S. Cl.
CPC ........ G01R 33/56366 (2013.01); A61B 5/026 (2013.01); A61B 5/055 (2013.01); A61B 5/7425 (2013.01); A61B 5/489 (2013.01); A61B 5/7285 (2013.01); A61B 2576/026 (2013.01); G01R 33/4824 (2013.01)

(58) Field of Classification Search
CPC .......... G01R 33/56366; G01R 33/4824; A61B 5/026; A61B 5/055; A61B 5/7425; A61B 5/489; A61B 5/7285; A61B 2576/026
See application file for complete search history.

(56) References Cited

U.S. PATENT DOCUMENTS

| 7,047,060 B1 * | 5/2006 | Wu | G01R 33/563 |
| | | | 324/307 |
| 7,283,862 B1 * | 10/2007 | Slavin | G01R 33/4835 |
| | | | 324/306 |
| 8,089,278 B1 * | 1/2012 | Du | G01R 33/4824 |
| | | | 324/307 |
| 2006/0226836 A1 * | 10/2006 | Shu | G01R 33/54 |
| | | | 324/309 |
| 2013/0123611 A1 * | 5/2013 | Riederer | G01R 33/4818 |
| | | | 600/419 |
| 2015/0327783 A1 * | 11/2015 | Wang | A61B 5/0263 |
| | | | 600/419 |

(Continued)

OTHER PUBLICATIONS

Kopeinigg et al., Time-Resolved Angiography Using InfLow Subtraction (TRAILS), Magn Reson Med. Sep. 2014; 72(3):669-678. doi:10.1002/mrm.24985. (Year: 2014).*

(Continued)

*Primary Examiner* — Amelie R Davis
*Assistant Examiner* — John Denny Li
(74) *Attorney, Agent, or Firm* — Thomas|Horstemeyer, LLP

(57) ABSTRACT

The present disclosure is directed to combined angiography and perfusion using radial imaging and arterial spin labeling.

25 Claims, 16 Drawing Sheets

(56) References Cited

U.S. PATENT DOCUMENTS

2017/0146627 A1* 5/2017 Cheng .............. G01R 33/56316
2017/0160365 A1* 6/2017 Helle ................ G01R 33/4838

OTHER PUBLICATIONS

Orkisz et al., Improved vessel visualization in MR angiography by nonlinear anisotropic filtering, Magn Reson Med. Jun. 1997; 37(6): 914-9. (Year: 1997).*

Wang et al., Empirical optimization of ASL data analysis using an ASL data processing toolbox: ASLtbx, Magn Reson Imaging. Feb. 2008; 26(2): 261-269. (Year: 2008).*

Lee et al., Rapid Time-Resolved Magnetic Resonance Angiography via a multi-echo radial trajectory and GraDeS reconstruction, Magn Reson Med. Feb. 2013; 69(2): 346-359. doi:10.1002/mrm.24256. (Year: 2013).*

* cited by examiner

COMBINED ANGIOGRAPHY AND PERFUSION USING RADIAL IMAGING AND ARTERIAL SPIN LABELING

CROSS-REFERENCE TO RELATED DOCUMENTS

This application claims priority to and the benefit of provisional application entitled "COMBINED ANGIOGRAPHY AND PERFUSION USING RADIAL IMAGING AND ARTERIAL SPIN LABELING," having Ser. No. 62/325,361, filed Apr. 20, 2016, which is incorporated herein by reference in its entirety.

This application makes reference to and incorporates by reference the following paper as if it were fully set forth herein expressly in its entirety.

Combined Angiography and Perfusion Using Radial Imaging and Arterial Spin Labeling, attached hereto as Appendix A.

TECHNICAL FIELD

The present disclosure generally relates to medical imaging and, more particularly, relates to systems and methods for providing clinicians with blood flow and tissue perfusion information to help make diagnostic, prognostic and/or therapeutic decisions.

BACKGROUND

Diseases that affect the blood supply to the brain are leading causes of death and disability in the USA [1]. Medical imaging techniques that visualize blood flow to the brain are important for accurate diagnosis, prognosis, and treatment decision-making [2]. In a variety of cerebrovascular diseases it is useful to have information about blood flow both at the level of the large arteries, to visualize stenoses, occlusions or abnormal vessels, and at the level of the tissue, to assess the effects on the resulting downstream perfusion. However, within a busy clinical protocol, the separate acquisition of angiographic and perfusion data may not be feasible.

Currently, many common methods for assessing blood flow through the arteries or tissue perfusion rely on injecting an exogenous contrast agent. Use of exogenous contrast agents is invasive, increases the scan set-up time, decreases patient comfort, and excludes some patients with contraindications to contrast agents. For example, Gadolinium-based contrast agents can be problematic when used in patients with kidney dysfunction [3]. Many methods also use ionizing radiation, with its associated risks, which limits the number of scans that each patient can undergo.

These needs have prompted the growth of arterial spin labeling (ASL) [4,5], a magnetic resonance imaging (MRI) based method that uses blood water as an endogenous tracer. ASL is an MRI method that can generate angiograms and tissue perfusion maps without ionizing radiation or contrast agents. Typically ASL is used to generate maps of blood flow at the tissue level (perfusion), which can be used for identifying brain regions that are at risk of permanent damage due to compromised blood supply.

To decide on the best course of treatment it is important to know the underlying cause of this deficit in the brain-feeding arteries. There have been recent investigations into the use of ASL to obtain this information by visualizing blood flowing through the arteries (angiography) [6-10, 40]. However, these methods often have limited spatial coverage or temporal resolution. ASL-based time-resolved 3D angiograms are currently very time-consuming to acquire and images of the tissue perfusion have to be acquired separately from angiograms, the perfusion data acquired after a time delay for blood to reach tissue. It is often not possible to perform both perfusion imaging and angiography in a single session due to limitations on the scan time that patients can tolerate, leaving the clinician with incomplete information. Increasing scan time can also generate undesirable artefacts in the data sets and resulting images, for example, due to subject motion or drift in scanner parameters. In addition, the timing of conventional ASL acquisitions must be decided in advance, meaning that images acquired in patients with very fast or slow blood flow may fail to capture important features.

Complete assessment of blood flow to the brain requires both knowledge of blood flow through the large arteries and perfusion at the tissue level. However, separate acquisition of dynamic angiograms and perfusion maps is time-consuming. One attempt to simultaneously acquire angiograms and perfusion maps without ionizing radiation or contrast agents has been published (Y. Suzuki, W. M. Teeuwisse, S. Schmid, P. Koken, M. V. Cauteren, M. Helle, and M. J. van Osch, "Simultaneous acquisition of perfusion maps and 4D MR angiography by means of arterial spin labeling MRI," in Proceedings 22nd Scientific Meeting, ISMRM, (Milan, Italy), p. 720, May 2014); see also, WO2015158879A1. In this method the authors use an ASL preparation combined with two separate image readout modules: one for angiography and one for perfusion imaging, each acquiring data differently. This approach, however, also has a number of disadvantages. This approach means that the image timing must be decided in advance at specific time points. In addition, their approach yields no dynamic information about blood flow into the tissue (tissue perfusion), making it potentially biased where blood flow is delayed, and the use of time-encoding intrinsically links the temporal resolution of the angiograms to the signal strength.

SUMMARY

Provided herein are MRI-based systems and methods to simultaneously generate dynamic images of blood flowing through the arteries and all the way into the tissue (tissue perfusion), yielding both dynamic angiograms and time-resolved perfusion maps non-invasively and without contrast or ionizing agents.

The present systems and methods have a number of advantages over those previously attempted. The present systems and methods can generate both dynamic angiograms and tissue perfusion maps from a single scan, increasing scan efficiency whilst also allowing a great deal of flexibility in the image reconstruction. The timing of the reconstructed angiographic and perfusion images does not need to be decided in advance and can be decided retrospectively, allowing adaptation to the blood flow rates in each individual patient.

The present systems and methods can use a continuous readout scheme which can allow both angiographic and perfusion images to be reconstructed from the same raw data set at any time-points within the acquisition window and with any desired temporal resolution. The present systems and methods can be adapted to the hemodynamics of each individual patient. The present systems and methods can minimize dropout and distortion artefacts often encountered in ASL perfusion imaging and can reduce such The present systems and methods can be applied to any organ in any living being that contains fluid in a vascular network that is perfused into tissue. The present systems and methods can be useful in the detection, prognosis, and therapeutic monitoring of a range of diseases, such as stroke, where blockages or narrowing of arteries, or vessels that supply fluid to tissue, could be assessed, along with the effect this has on perfusion to the tissue. The present systems and methods can also be useful for assessing blood supply to tumours or arteriovenous malformations, amongst other diseases. The present systems and methods can be used in a longitudinal manner, and can be used to evaluate patients before, during, and after disease detection and resulting therapy.

In an embodiment, implementation of combined angiography and perfusion using radial imaging and arterial spin labeling (CAPRIA) sequence is provided. The CAPRIA sequence allows reconstruction of whole-brain dynamic angiograms and time-resolved perfusion maps from the same raw data set. In addition, a variable flip angle imaging scheme is shown to benefit the visualization of tissue perfusion without compromising angiographic image quality. The angiographic and perfusion images can be constructed in 2D, 3D or even 4D. In an aspect, a full 4D (time-resolved 3D) implementation is provided to obtain whole brain dynamic angiograms and perfusion maps within a single scan.

In an embodiment, the present systems and methods can use an arterial spin labeling (ASL) preparation to label the blood followed by a continuous golden ratio (also referred to as golden angle) radial readout scheme to continuously image the labeled blood all the way through the large arteries and into the tissue. Images can also be acquired where the blood is not labeled (control images). Subtraction of images with and without labeling of the blood removes all of the signal from the tissue, leaving only an image containing the blood signal. The use of the golden angle or ratio scheme provides that the same raw data set can be reconstructed at different temporal and spatial resolutions that can be chosen retrospectively. In various aspects, angiographic and perfusion images can be constructed in 2D, 3D or even 4D. In various aspects, imaging data can be combined across multiple ASL preparation periods to increase the amount of data available for image reconstruction.

In various aspects, angiographic images can be reconstructed at high temporal resolution, using a relatively high undersampling factor, to show the rapid dynamics of blood flowing through the arteries. These images can be well suited to undersampling due to their sparse nature and relatively high signal-to-noise ratio (SNR). The dynamics of blood flow into the tissue (perfusion) can be slower, but the SNR can be poorer, and the images can be less sparse, so a broader temporal resolution can be used to reduce the undersampling factor and boost the SNR. In addition, the spatial resolution required for perfusion imaging can be lower, so images can be reconstructed using just the central portion of k-space (the domain in which raw MRI data are acquired), which can be more heavily sampled by the radial acquisition scheme, which can boost the SNR further. Alternatively, perfusion images can be reconstructed at the same spatial resolution as the angiographic images but spatial smoothing can subsequently be applied to the images to boost the SNR. For angiographic images, if the ASL preparation is performed over a period of time long enough that the labeled blood water has already filled the major arteries, inflow subtraction, in which all image frames are separately subtracted from the first, can be used in post-processing to generate images that give the appearance of blood flowing into the imaging region [41, 42].

As mentioned above the present systems and methods can be applied to any organ in the body, with appropriate adaptations (e.g. cardiac/respiratory gating) if necessary. The systems and methods can be compatible with various ASL techniques, such as pseudo-continuous ASL, pulsed ASL, time-encoded (also called Hadamard encoded) and vessel-selective ASL methods that allow separate images of blood flow arising from each feeding artery to be generated. The present system and methods can be used for visualizing phenomena such as collateral flow, which is correlated with better outcomes in stroke patients, and identifying the blood supply to lesions, such as arteriovenous malformations or tumours. A similar approach can also be used in contrast-enhanced MRI studies to image the passage of the contrast agent through the arteries and into the tissue, yielding dynamic angiograms and maps of tissue perfusion.

In an embodiment, a computer implemented method for combined angiography and perfusion using arterial spin labeling and radial imaging is provided. The method can comprise the steps of: labeling blood for dynamic imaging with arterial spin labeling; acquiring a data set from the labeled blood using radial imaging and a continuous readout scheme; reconstructing one or more angiography images from the data set, wherein the one or more reconstructed angiography images are reconstructed with a spatial and temporal resolution appropriate for angiography; and reconstructing one or more perfusion images from the data set, wherein the one or more reconstructed perfusion images are reconstructed with a spatial and temporal resolution appropriate for perfusion imaging.

In an embodiment, a system for combined angiography and perfusion imaging is provided. The system can comprise: at least one computing device; at least one application executable in the at least one computing device, the at least one application comprising logic that when executed in the at least one computing device:
  A. labels blood for dynamic imaging with arterial spin labeling;
  B. acquires data from the labeled blood set using radial imaging and a continuous readout scheme;
  C. reconstructs one or more angiography images from the data set, wherein the one or more reconstructed angiography images are reconstructed with a spatial and temporal resolution appropriate for angiography; and
  D. reconstructs one or more perfusion images from the data set, wherein the one or more reconstructed perfusion images are reconstructed with a spatial and temporal resolution appropriate for perfusion imaging.

In any one or more aspects of any one or more embodiments, the arterial spin labeling can be pseudo-continuous ASL, time-encoded (also known as Hadamard encoded) ASL, pulsed ASL, or vessel-selective ASL. The radial imaging can include incrementing an azithumal angle, and the azithumal angle, increment can be constant. The azithumal angle can be 111.2 degrees for 2D imaging. The angiography temporal resolution can be higher than the perfusion temporal resolution. The angiography temporal resolution can be in the range of 5 to 2000 ms, preferably about 100 ms. The perfusion temporal resolution can be in the range of 5 to 2000 ms, preferably about 250 ms.

In any one or more aspects of the system, the logic further comprises logic that:
  processes the one or more reconstructed angiography images with inflow subtraction. The logic can include logic that:

processes the reconstructed angiography images with post-hoc spatial smoothing. The logic can include logic that:

processes the reconstructed perfusion images with post-hoc spatial smoothing.

In any one or more aspects of any one or more of the embodiments, the acquired data can be used to estimate and correct for subject motion and drift in scanner parameters (such as drift in the main magnetic field strength). For example, a series of low spatial resolution but high temporal resolution images can be reconstructed from the data and used to estimate the subject motion. These motion estimates can be used to correct for motion in the image reconstruction process. A similar process can for magnetic field drift, where the drift can be estimated from a central region of k-space (or even just the central point in k-space) with high temporal resolution and corrected for during image reconstruction. Variable flip angles for imaging can be used.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 6A-6C depict angiographic and perfusion signal simulations comparing constant flip angle (CFA) and variable flip angle (VFA) approaches, in which FIG. 6A depicts a CFA and a VFA schedule, FIG. 6B depicts an angiographic signal, and FIG. 6C depicts a perfusion signal.

DETAILED DESCRIPTION

Figure 1:
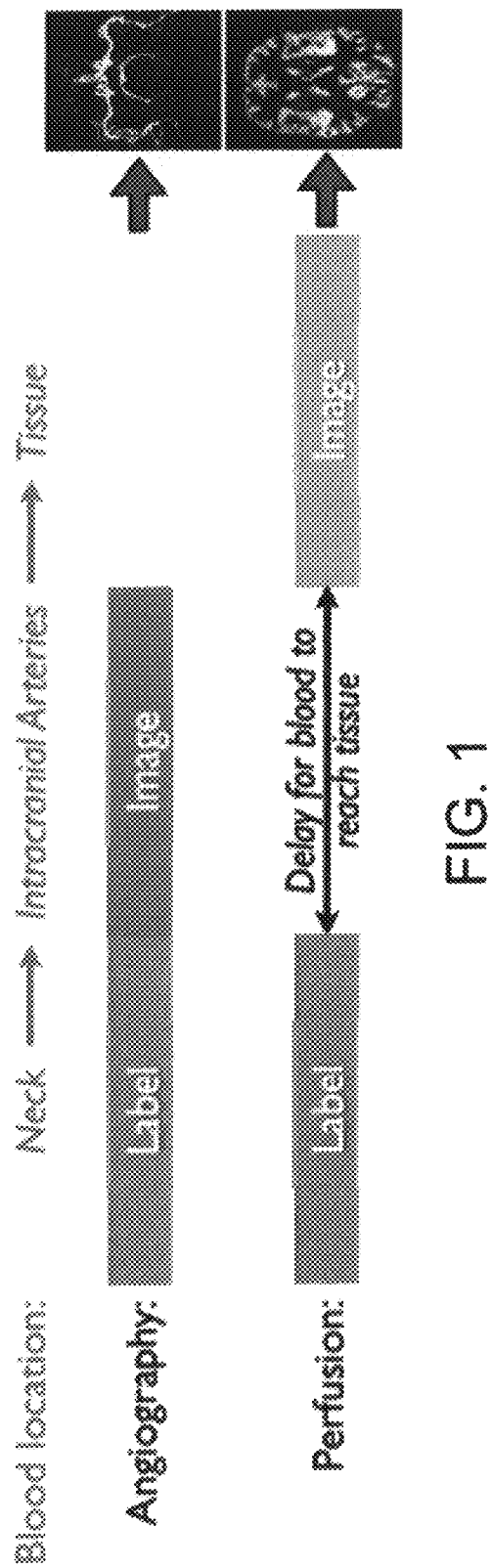
FIG. 1 depicts a prior art method of separate acquisition of angiography and perfusion data.

Described below are various embodiments of the present systems and methods for combined angiography and perfusion using radial imaging and arterial spin labeling (CAPRIA). Although particular embodiments are described, those embodiments are mere exemplary implementations of the system and method. One skilled in the art will recognize other embodiments are possible. All such embodiments are intended to fall within the scope of this disclosure. Moreover, all references cited herein are intended to be and are hereby incorporated by reference into this disclosure as if fully set forth herein. While the disclosure will now be described in reference to the above drawings, there is no intent to limit it to the embodiment or embodiments disclosed herein. On the contrary, the intent is to cover all alternatives, modifications and equivalents included within the spirit and scope of the disclosure.

Discussion

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Description

In conventional arterial spin labeling (ASL)[11-13], the inversion of blood water, for example in the neck, can be followed by a long post-labeling delay (PLD) to allow the blood to reach the tissue before separate image acquisition. When such images are subtracted from "control" images, in which the blood water was not inverted, images of perfusion can be obtained. ASL can also be used to generate angiographic images [14,15] if the PLD is very short. In cerebrovascular disease and other diseases relating to changes in blood flow and perfusion, information about the status of the arteries and tissue perfusion are both important, but separate angiographic and perfusion acquisitions can be unfeasible in a busy clinical protocol.

In an embodiment, a continuous imaging approach is provided herein where the labeled blood can be tracked throughout its path from vessels all the way into tissue. In an aspect, labeled blood can be tracked throughout its path from the neck all the way into the brain tissue. In this manner angiographic images can be reconstructed from data acquired soon after labeling, and perfusion images obtained from later time points but from the same data. This not only represents a considerable boost in efficiency and increased clinical patient throughput, since both sets of images can be acquired from a single scan, but also can increase flexibility. For example, in patients with arterial disease the blood can take considerably longer to reach the tissue than would normally be expected. This can be problematic for standard angiographic techniques where useful information lies outside the time window normally used for imaging, but with the proposed approach angiographic images can be generated at any desired time point. This also provides the opportunity to visualize delayed compensatory blood flow through small collateral vessels, which has a high clinical significance [16].

In various aspects of the present disclosure, angiography and perfusion imaging are not utilized as separate techniques, but as different windows on a continuous process of blood flow, for example blood flowing into the brain. Conventionally, angiography is performed immediately after the ASL labeling period whilst the blood is still within the large arteries and has fast temporal dynamics, whereas perfusion imaging would occur separately following a delay for the labeled blood to reach the brain tissue, as depicted in FIG. 1.

In an embodiment, a new golden ratio radial arterial spin labeling acquisition method is provided in which labeled blood water is continuously imaged as it passes through the large arteries, related downstream vasculature, and into the tissue. Both angiographic and perfusion images can then be reconstructed from the same raw data set at any retrospectively chosen time points and temporal resolution. This makes efficient use of the aforementioned post-labeling delay (PLD) dead time to provide a more complete assessment of blood flow, for example into the brain, which can be of use in diagnosing a variety of cerebrovascular diseases. A golden ratio radial arterial spin labeling acquisition method can also be used for the generation of 3D angiograms and perfusion data.

Figure 2A:
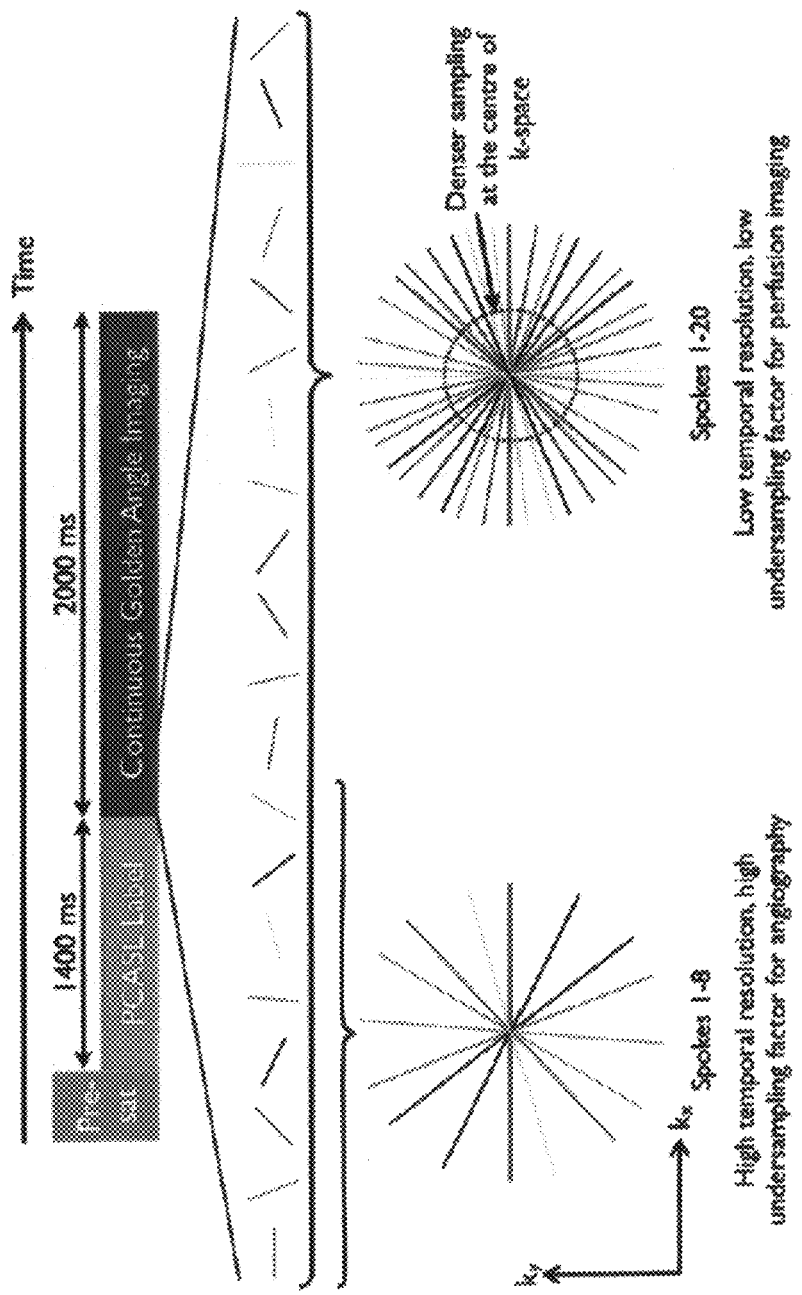
FIG. 2A is a schematic of an embodiment of the present disclosure. After pre-saturation and PCASL labeling, continuous golden angle radial imaging can allow for the reconstruction of both angiographic and perfusion images from the same raw data, using high and low temporal/spatial resolutions, respectively.
Figure 2B:
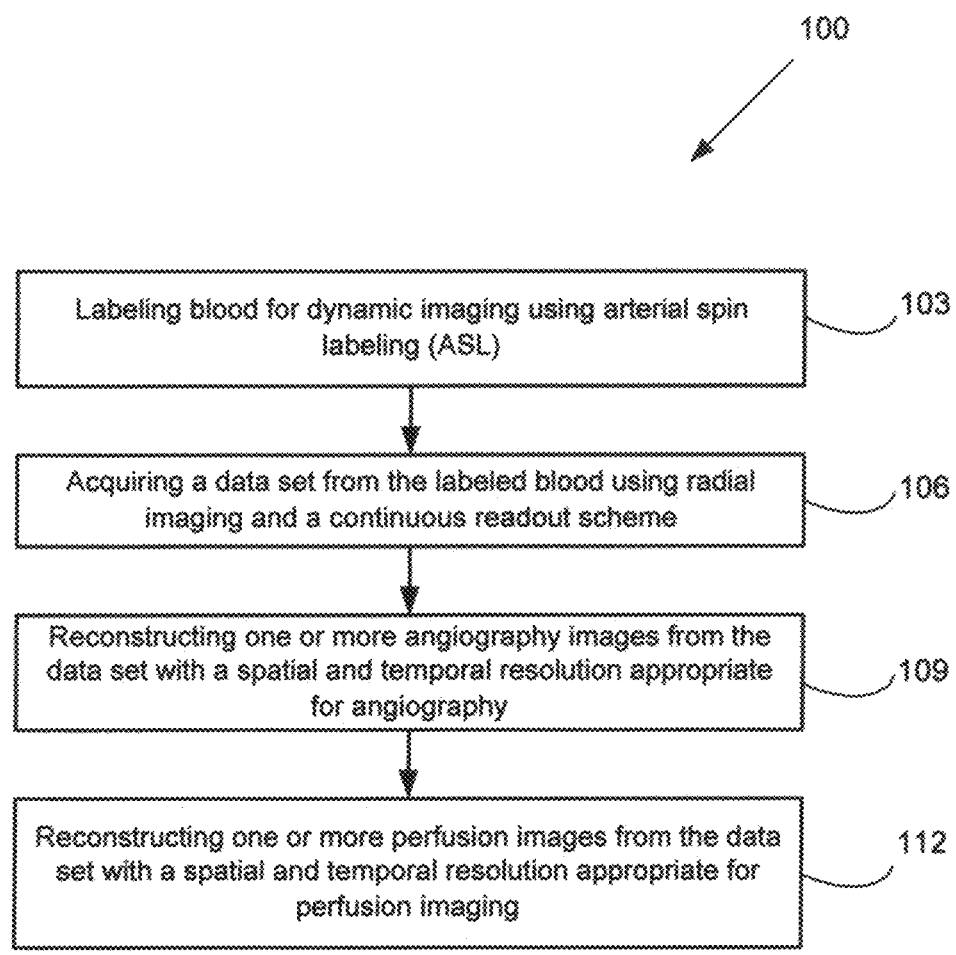
FIG. 2B is a flow chart of a method of the present disclosure.

A schematic of an embodiment of the present methods, that we call the Combined Angiography and Perfusion using Radial Imaging and ASL (CAPRIA) sequence, is shown in as a 2D implementation in FIG. 2A along with a flow chart of an exemplary method 100 in FIG. 2B. In one or more embodiments, we can apply background suppression. This can consist of utilizing a pre-saturation module, as shown in FIG. 2A. After pre-saturation, blood can be labeled using arterial spin labeling (ASL), e.g., using an ASL module. In the embodiment of FIGS. 2A and 2B pseudo-continuous ASL (PCASL) labeling 103 used. A data set can be acquired from the labeled blood. Optionally, additional inversion pulses can be used that act during or after the ASL module. The data set can be acquired from the labeled blood using radial imaging and a continuous readout scheme 106. A spoiled gradient echo golden angle radial scheme [17] can be used to continuously image the labeled blood passing through the arteries and into the tissue. One skilled in the art will recognize, however, that a spoiled gradient (SPGR) echo technique need not be used and that other techniques such as a balanced steady-state free precession (bSSFP) and fast imaging with steady-state free precession (FISP) techniques can be used. For conventional PCASL, control images can also be acquired. The subtraction of label and control images removes tissue signal to leave only the blood signal. Acquisition of control images with an identical imaging scheme will help to remove tissue signal in the resulting subtraction images, but alternative imaging schemes are also possible, particularly when used in conjunction with more advanced imaging reconstruction techniques, described below. Similarly other arterial spin labeling (ASL) techniques can be used as described elsewhere herein. Also, data for the data set can be collected after multiple, separate ASL preparation periods until the desired amount of data has been collected.

The golden angle radial imaging allows reconstruction of both angiographic and perfusion images from the same raw data set. One or more angiography images can be reconstructed from the data set with spatial and temporal resolution appropriate for angiography 109. Further, one or more perfusion images can be reconstructed from the same data set using a spatial and temporal resolution appropriate for perfusion imaging 112. The data can be sampled in the spatial frequency, or Fourier domain, often referred to as k-space. Many ASL preparations can be performed to obtain a greater number of samples in k-space for both label and control images. Once sampling of the k-space is completed, images can be reconstructed in a variety of ways, as described in more detail below. Sampling the data along radial spokes (the radial imaging) that pass through the center of the k-space allows for the reconstruction of high spatial and temporal resolution ASL angiograms that can be produced using only a fraction of the data normally required. This is shown, for example, by spokes 1-8 in the lower left portion of FIG. 2A. Lower spatial and temporal resolution, with a correspondingly lower undersampling factor, allows for perfusion imaging from the same data set. For example, perfusion images can be reconstructed from a larger number of radial spokes with denser sampling at the center of the k-space as depicted by the image of spokes 1-20 in the lower right portion of FIG. 2A. However, the image reconstruction process is totally flexible, so the desired spatial and temporal resolution used for reconstruction of angiographic or perfusion images can be decided retrospectively.

In various aspects, for example in 2D imaging as depicted in FIG. 2A, the radial imaging can begin by the readout of data along the horizontal radial spoke passing through the center of the k-space (passing through the center of the k-space at the 3 o'clock and 9 o'clock positions). Further sampling can occur at various azimuthal radial angles about the center of the k-space. As described in the Example below, the next sampling can occur at as azimuthal angle of about 111.2°, derived from the golden ratio [22], from the horizontal radial spoke and at similar azimuthal angular increments therefrom. This is depicted in the middle portion of FIG. 2A wherein from left to right a first sampling is taken along the horizontal radial spoke. The next sample (to the right in the figure) is taken along a radial spoke incremented by 111.2° from the horizontal spoke and each following sample occurring at similar 111.2° increments from the previous spoke. One skilled in the art will recognize, however, that the azimuthal angle need not be incremented at 111.2° or even at exactly 111.2°, and that other azimuthal angular increments, which can be non-linear or (pseudo)-random, can be used. Further, FIG. 2A depicts a 2D acquisition in a plane.

Figure 4:
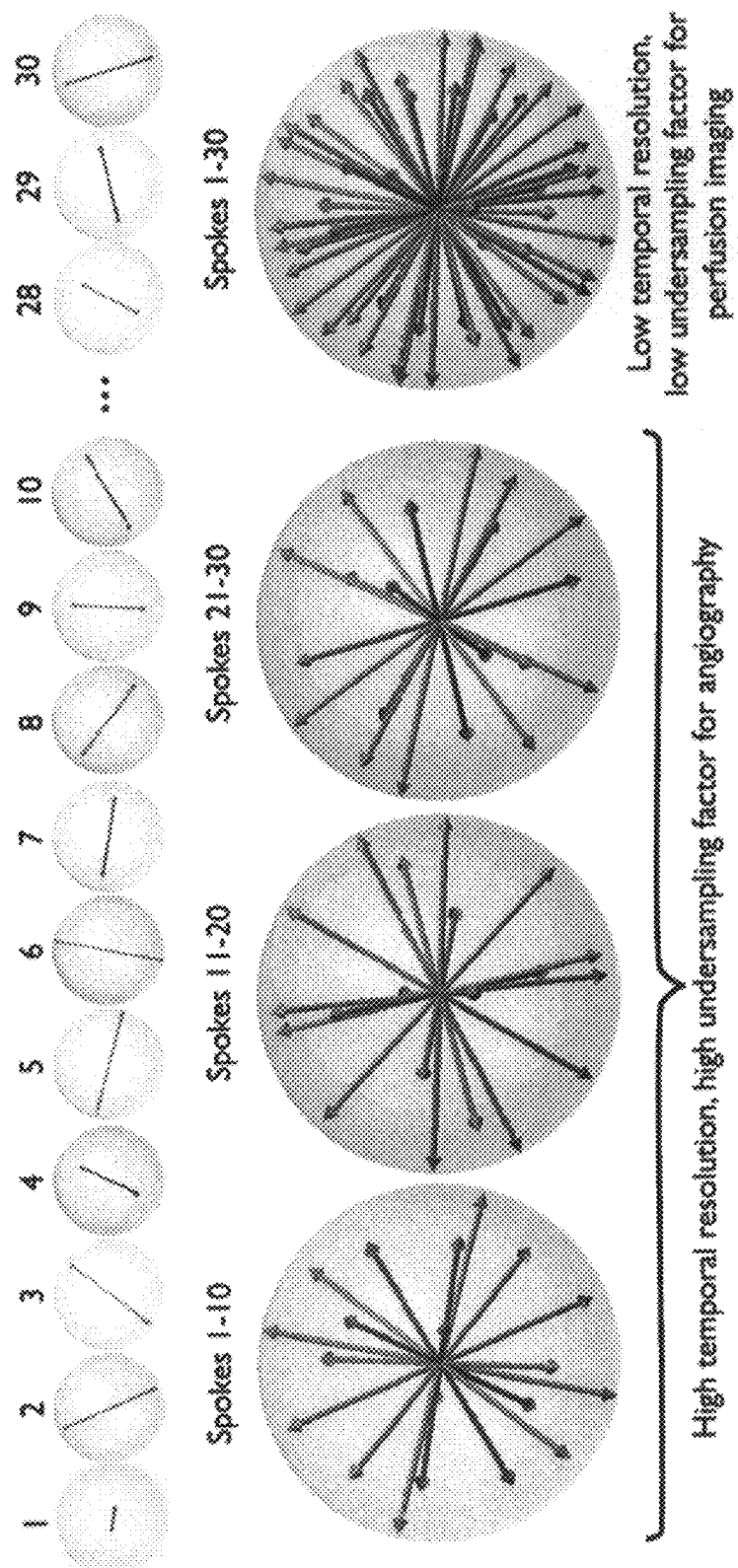
FIG. 4 is a schematic of a 3D pulse sequence in accordance with the present disclosure.

3D acquisitions can also be acquired, such as depicted in FIG. 4 in which the radial samples are not taken in a plane but instead within a sphere of k-space. In this case, the radial spokes can be acquired according to increments determined by the golden ratio although other sampling strategies are also possible, including non-linear increments and (pseudo)-random sampling. A full 4D (time-resolved 3D) acquisition can also be implemented, as discussed in more detail below.

By reconstruction of both angiographic and perfusion images from the same raw data set using high and low temporal resolutions, respectively, in one or more aspects we mean the temporal resolution of the angiography image is high compared to the temporal resolution of the perfusion image. In various other aspects, by a "high" temporal resolution in reference to the angiographic image(s) we mean a temporal resolution in the range of 5 ms to 2000 ms, preferably approximately 50 ms to about 200 ms. By a "low" temporal resolution for the reconstruction of the perfusion image(s), in various aspects, we mean a resolution within the range of about 50 ms to 3000 ms, preferably about 250 ms. By "high" spatial resolution, we mean the maximum spatial resolution allowed by the k-space sampling scheme used. By "low" spatial resolution, we mean only a subset of the k-space samples are used for the image reconstruction, within the range 10% to 100% of the k-space samples, where post-hoc spatial smoothing may also be used to reduce the effective spatial resolution and boost the SNR in post-processing.

Figure 3:
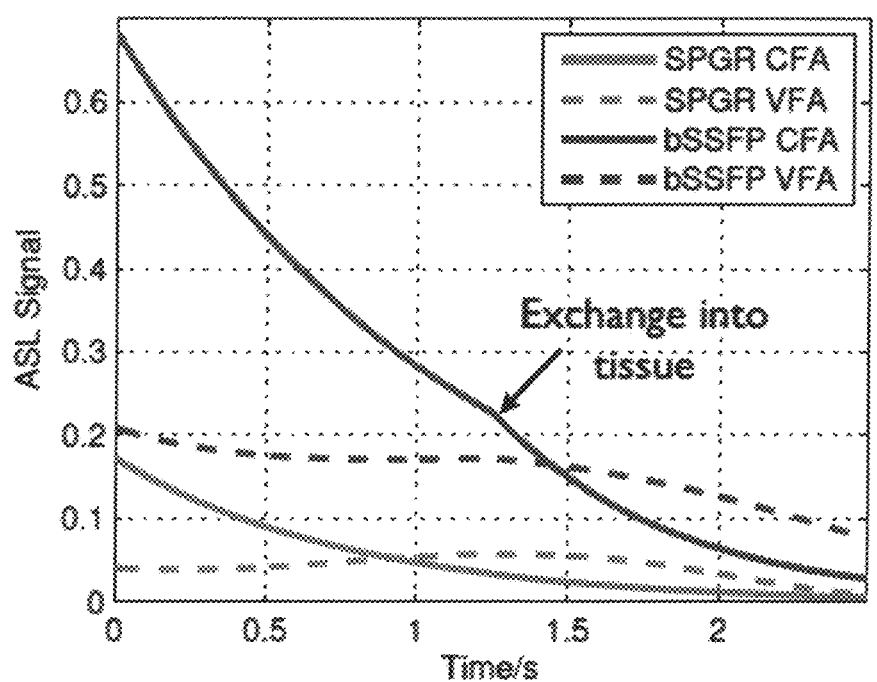
FIG. 3 illustrates preliminary simulations of an ASL signal resulting from an example acquisition. Two example imaging schemes are simulated: balanced steady-state free precession (bSSFP) and spoiled gradient echo (SPGR). bSSFP can result in stronger signals than SPGR. Variable flip angle (VFA) schemes can give a more consistent signal strength over time compared to constant flip angle (CFA) schemes. In the example, it is assumed the labeled water exchanges into tissue at 1.25 s, resulting in a small deviation in the shape of the curves.

In some imaging schemes according to the present disclosure, the ASL signal may be rapidly attenuated, leading to poor SNR at later time points. This may be particularly problematic for spoiled gradient echo (SPGR) techniques [18], because part of the ASL signal may be destroyed each time it is sampled. This effect can be much less exaggerated for methods based on highly efficient balanced steady-state free precession (bSSFP) [19], meaning that high SNR can be sustained over a longer period of acquisition time (FIG. 3). However, bSSFP is more sensitive to magnetic field inhomogeneity introduced by the presence of the patient in the scanner. In addition, high signal strength can be maintained at later time points by varying the flip angle of the radio-frequency (RF) pulses used to generate the MRI signal, at the cost of lower signal strength at earlier time points [20]. A similar trade-off may be involved for the RF pulse repetition time, TR: a short TR means data are acquired more rapidly, at the cost of greater signal attenuation. Simulations can be used to optimize the variable flip angle schedule and other image acquisition parameters to reduce signal attenuation, ensure high SNR, and robustness to field inhomogeneity. Constant flip angles or variable flip angles can be used in the herein described system and method.

The different spatial and temporal resolution requirements of angiography and perfusion imaging can present challenges, and attention can be applied to the data sampling strategy in view of these challenges. In MRI, data are sampled in the spatial frequency, or Fourier, domain, often referred to as k-space. Once k-space is fully sampled, images can be reconstructed via the discrete Fourier Transform. Conventionally, data in k-space are sampled uniformly on a Cartesian grid, but this can lead to long acquisition times if high spatial resolution is required. If data are acquired along radial spokes that pass through the center of k-space [21], then high resolution ASL angiograms (2D and 3D) can be produced using only a fraction of the data normally required [10]. It can also be possible to acquire these radial spokes in such a manner that within any arbitrary time window the data can be evenly sampled throughout k-space [22, 23]. Thus, images can be reconstructed at high temporal resolution with a high undersampling factor, or at lower temporal resolution with a lower undersampling factor (an example of 2D continuous golden angle imaging scheme is shown in FIG. 2.

Figure 12:
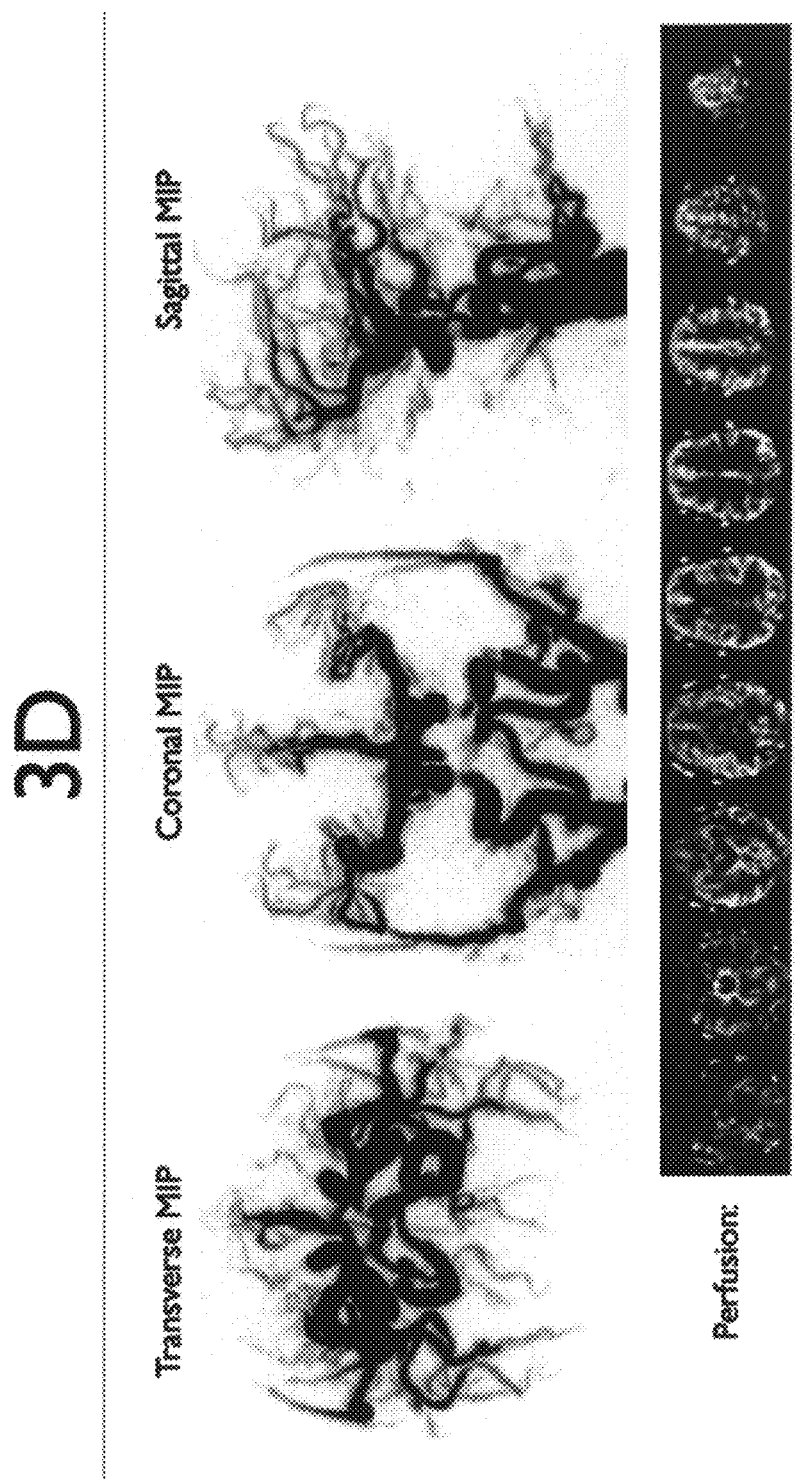
FIG. 12 is an example of 3D acquisition of angiograms and perfusion maps in accordance with the present disclosure.

An example of 3D continuous golden ratio imaging scheme is shown in FIG. 4, which can be suitable for the unified acquisition presented herein. The grey sphere in FIG. 4 represents the region of k-space that can be sampled. The grey lines represent individual spokes along which data points can be acquired. Any given subset of consecutively acquired spokes can be evenly spaced throughout the sphere, allowing flexible image reconstruction. In this example, thirty spokes can be reconstructed as three highly under sampled images with high temporal resolution, ideal for angiography. Alternatively, the same data can be used to generate a single image with less under sampling but lower temporal resolution, and can be used for perfusion imaging. For the 3D imaging, two angles are modified in a slightly more complex manner than for 2D imaging as described herein [22,23]. An example of 3D CAPRIA data are shown in FIG. 12.

Figure 5:
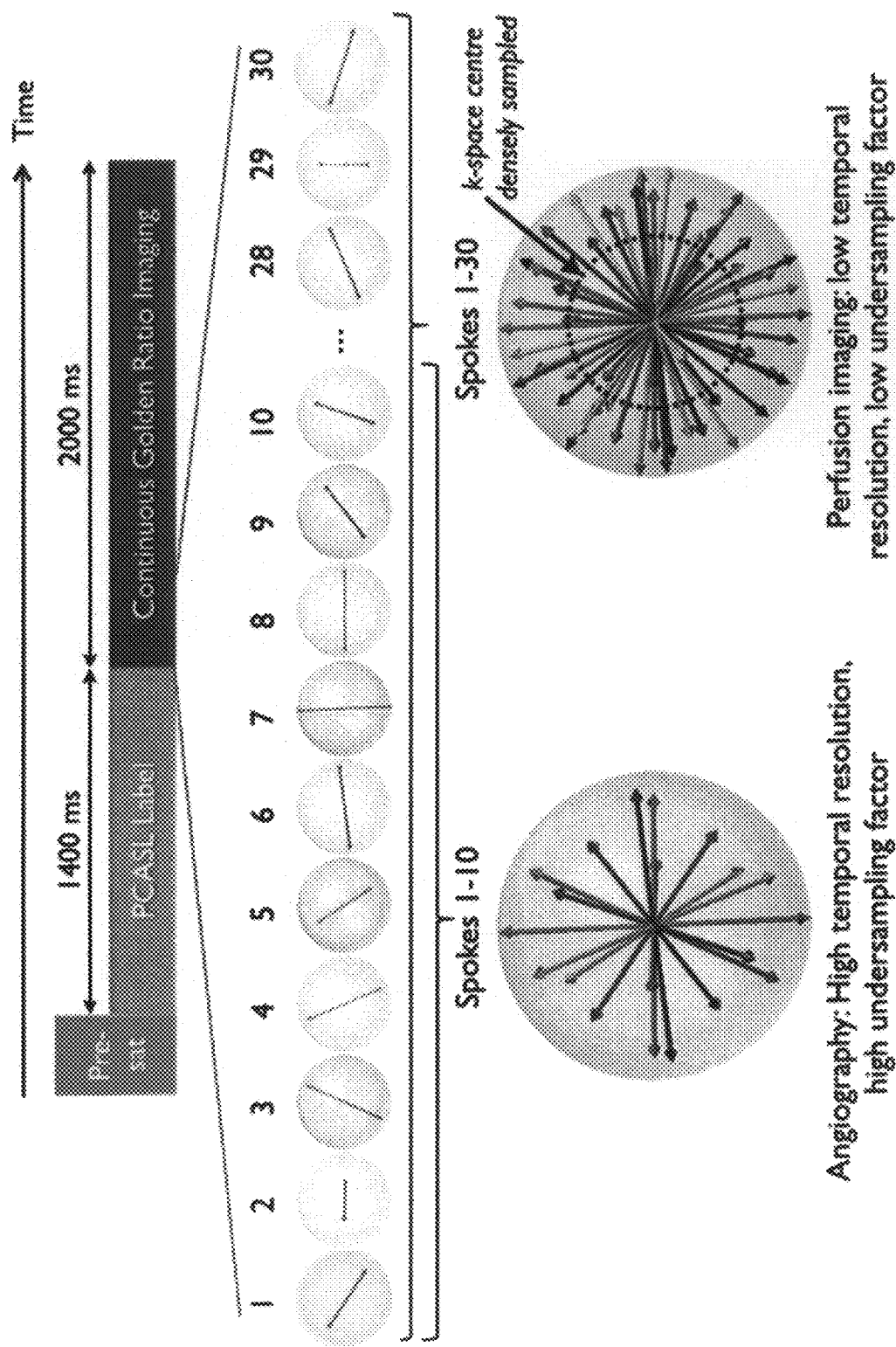
FIG. 5 is a schematic of an implementation of a 4D pulse sequence in accordance with the present disclosure.
Figure 13:
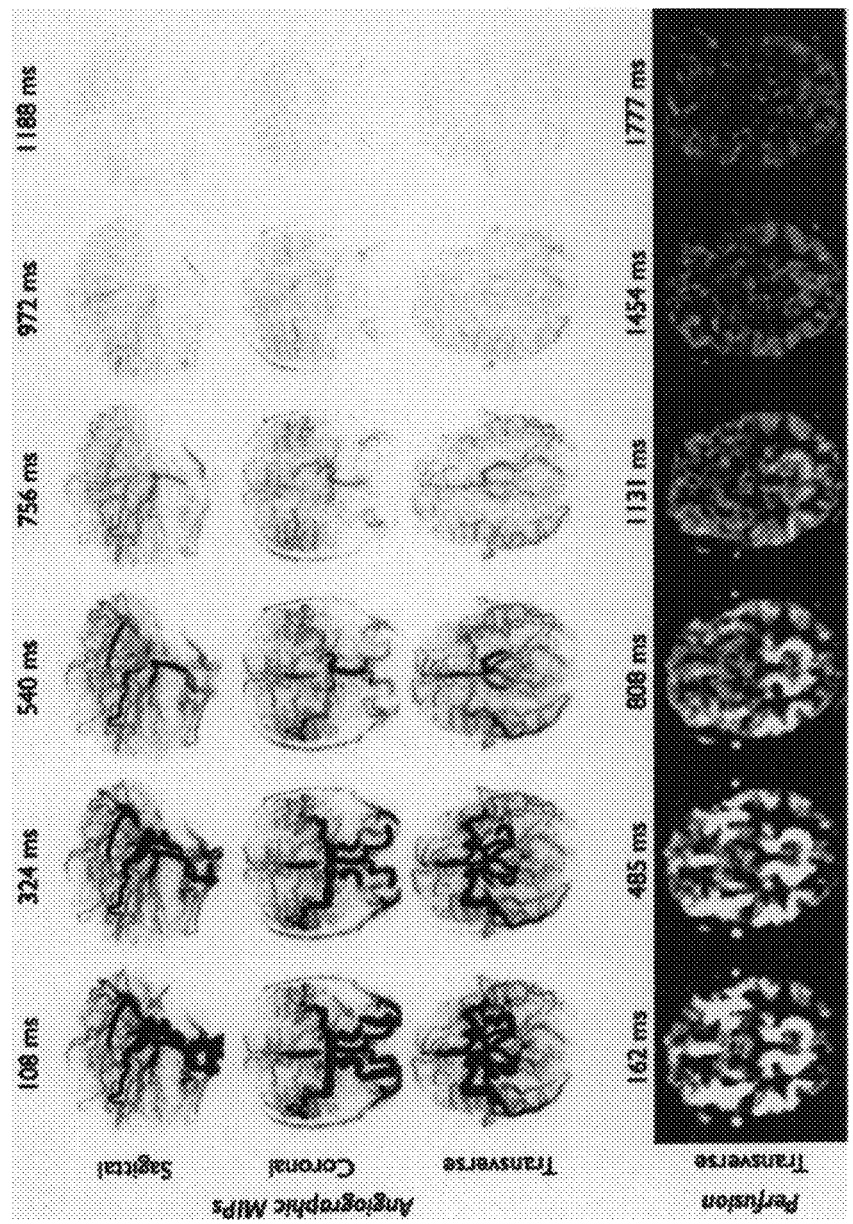
FIG. 13 is an example of 4D acquisition of angiograms and perfusion maps in accordance with the present disclosure.

A schematic of a 4D CAPRIA pulse sequence of the present disclosure is shown in FIG. 5. Pre-saturation can be used for background suppression. Pseudocontinuous ASL (PCASL) labeling can generate the bolus of labeled blood. A spoiled gradient-echo golden ratio radial scheme [23] can continuously image the labeled blood as it passes through the vascular network and into the tissue. This approach ensures that within any arbitrary temporal window the acquired data are evenly spread throughout 3D k-space, even when combining across multiple PCASL preparations. This enables the reconstruction of angiographic images at high temporal resolution and perfusion images at lower temporal resolution from the same raw data set. Subtraction artefacts (e.g. from subject motion) can be minimized by interleaving the acquisition of label and control data. An example of 4D CAPRIA data are shown in FIG. 13.

Figure 6C:
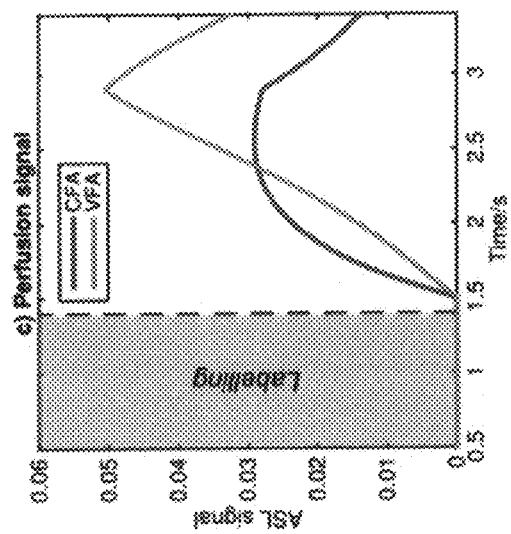
Figure 6B:
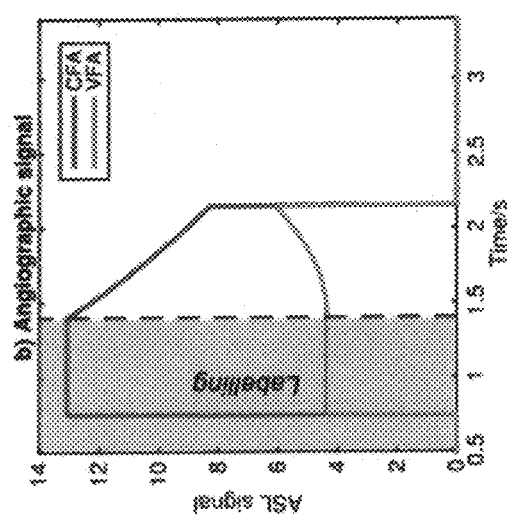
Figure 6A:
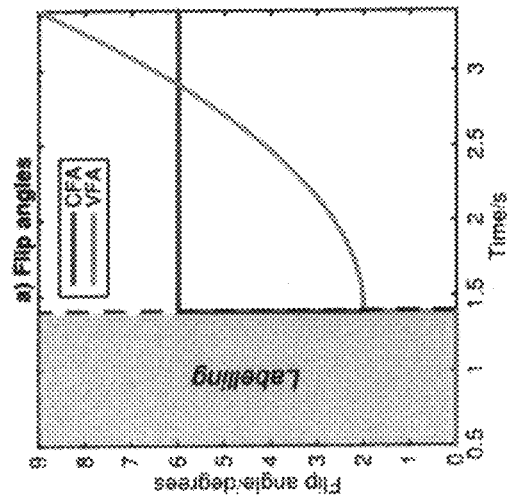

Due to T1 decay of the labeled blood, attenuation of the ASL signal by the imaging RF pulses, and the lower concentration of blood at the tissue level, the perfusion signal is considerably weaker than the angiographic signal. To compensate, a variable flip angle (VFA) scheme was considered in which the imaging flip angle increases quadratically during the acquisition period [20]. Numerical simulations of the ASL angiographic [32] and perfusion [24] signals, accounting for RF attenuation, were used to compare VFA and constant flip angle (CFA) approaches (FIG. 6). One skilled in the art will recognize that other schemes can be implemented in which the flip angle is varied.

The present approach is not limited to use of pseudo-continuous ASL (PCASL) labeling. In various aspects, other ASL labeling techniques can be used. These can include the use of a pulsed ASL preparation of labeling, time-encoded (also known as Hadamard encoded) ASL, and a vessel-selective ASL preparation or labeling in which the blood in each feeding artery can be uniquely encoded allowing their contributions to the downstream signal to be extracted in post-processing [25]. This can allow imaging of collateral blood flow [16] and arterial supply to lesions [26], but can also lead to increases in scan time because the number of encoded images required is proportional to the number of arteries of interest. This can be mitigated by leveraging the mutual information shared by the differently encoded images to enable a greater degree of undersampling. The radial sampling scheme described herein is well suited to estimation and correction for patient motion. For example, a series of high temporal resolution but low spatial resolution images can be reconstructed, allowing estimation of the subject's position at each point in time. This information can then be incorporated into the image reconstruction to correct for this motion. Alternatively, brief "navigator" scans can be interleaved with the main acquisition to provide an estimate of patient motion, thereby enabling prospective motion correction [27]. This can be important for stroke patients, who can be disoriented and uncomfortable, leading to potentially large motion artefacts if not properly addressed.

Radial images in 2D, 3D, or 4D can be reconstructed using standard techniques, such as weighting to correct for the non-uniform density of k-space samples, regridding of the samples on to a Cartesian grid and then application of the discrete Fourier transform. When there is a high degree of undersampling this can lead to significant "noise-like" artefacts in the resulting images [21]. "Compressed sensing" techniques can be introduced that allow highly under sampled images to be reconstructed with high fidelity by using iterative, sparsity-promoting algorithms [29]. Such techniques can be suitable for angiography because the images can be inherently sparse in both the spatial and temporal frequency domains, allowing highly under sampled data to be reconstructed accurately. In addition, the radial trajectories provided herein can be well suited to this methodology since undersampling can result in noise-like errors rather than coherent artefacts, which can enable the algorithms to disentangle the true signal amidst the noise. Perfusion data can be less sparse in the spatial domain, but the degree of undersampling can be smaller due to the lower temporal resolution required. In addition, the spatial resolution required can also be lower, so images can be reconstructed from a smaller region near the center of k-space where the sampling density of the radial spokes is greater, or additional smoothness constraints can be added to better condition the image reconstruction, or post-hoc spatial smoothing can be used. A range of other image reconstruction techniques can also be used that take advantage of the low rank nature of the data, or that regularize the reconstruction in other ways, for example, by using mathematical models of the expected signal evolution to constrain the reconstruction.

Therefore, provided herein is a flexible image reconstruction framework which can utilize compressed sensing, or similar techniques to allow the reconstruction of high spatial and temporal resolution angiographic images and lower resolution perfusion images at any time point following labeling. The flexible nature of this framework can allow the image reconstruction to adapt to the blood flow dynamics of each patient, yielding "patient-optimized compression".

System and Apparatus

Figure 7:
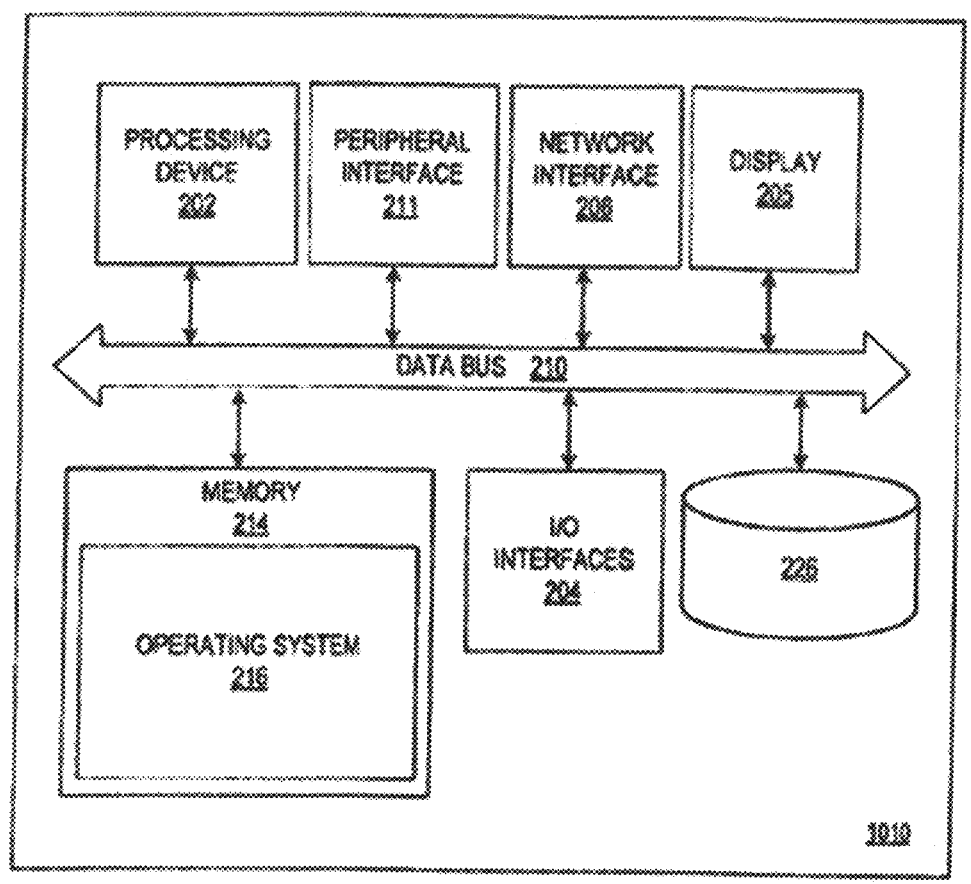
FIG. 7 is a schematic block diagram of an apparatus in which embodiments of the present systems and methods for combined angiography and perfusion imaging may be implemented.

Reference is now made to FIG. 7, which depicts an apparatus 1010 in which the systems and methods for combined angiography and perfusion imaging described herein may be implemented. The apparatus 1010 may be embodied in any one of a wide variety of wired and/or wireless computing devices, multiprocessor computing device, and so forth. As shown in FIG. 7, the apparatus 1010 comprises memory 214, a processing device 202, one or more input/output interfaces 204, a network interface 206, a display 205, a peripheral interface 211, and mass storage 226, wherein each of these devices are connected across a local data bus 210. The apparatus 1010 may be coupled to one or more peripheral measurement devices (not shown) connected to the apparatus 1010 via the peripheral interface 211.

The processing device 202 may include any custom made or commercially available processor, a central processing unit (CPU) or an auxiliary processor among several processors associated with the apparatus 1010, a semiconductor based microprocessor (in the form of a microchip), a macroprocessor, one or more application specific integrated circuits (ASICs), a plurality of suitably configured digital logic gates, and other well-known electrical configurations comprising discrete elements both individually and in various combinations to coordinate the overall operation of the computing system.

The memory 214 can include any one of a combination of volatile memory elements (e.g., random-access memory (RAM, such as DRAM, and SRAM, etc.)) and nonvolatile memory elements (e.g., ROM, hard drive, tape, CDROM, etc.). The memory 214 typically comprises a native operating system 216, one or more native applications, emulation systems, or emulated applications for any of a variety of operating systems and/or emulated hardware platforms, emulated operating systems, etc. For example, the applications may include application specific software which may be configured to perform some or all of the systems and methods herein. In accordance with such embodiments, the application specific software is stored in memory 214 and executed by the processing device 202. One of ordinary skill in the art will appreciate that the memory 214 can, and typically will, comprise other components which have been omitted for purposes of brevity.

The one or more input/output interfaces 204 provide any number of interfaces for the input and output of data. For example, where the apparatus 1010 comprises a personal computer, these components may interface with one or more user input devices 204. The display 205 may comprise a computer monitor, a plasma screen for a PC, a liquid crystal display (LCD) on a hand held device, a touch screen or other display device.

In an embodiment of this disclosure, a non-transitory computer-readable medium stores programs for use by or in connection with an instruction execution system, apparatus, or device. More specific examples of a computer-readable medium may include by way of example and without limitation: a portable computer diskette, a random access memory (RAM), a read-only memory (ROM), an erasable programmable read-only memory (EPROM, EEPROM, or Flash memory), and a portable compact disc read-only memory (CDROM) (optical).

With further reference to FIG. 7, network interface device 206 comprises various components used to transmit and/or receive data over a network environment. For example, the network interface 206 may include a device that can communicate with both inputs and outputs, for instance, a modulator/demodulator (e.g., a modem), wireless (e.g., radio frequency (RF)) transceiver, a telephonic interface, a bridge, a router, network card, etc.). The apparatus 1010 may communicate with one or more computing devices (not shown) via the network interface 206 over the network 118 (not shown). The apparatus 1010 may further comprise mass storage 226. The peripheral 211 interface supports various interfaces including, but not limited to IEEE-1394 High Performance Serial Bus (Firewire), USB, a serial connection, and a parallel connection.

The apparatus 1010 shown in FIG. 7 may be embodied, for example, as a magnetic resonance apparatus, which includes a processing module or logic for performing conditional data processing, and may be implemented either off-line or directly in a magnetic resonance apparatus. For such embodiments, the apparatus 1010 may be implemented as a multi-channel, multi-coil system with advanced parallel image processing capabilities, and direct implementation makes it possible to generate images, for example, immediate T1 maps, available for viewing immediately after image acquisition, thereby allowing re-acquisition on-the-spot if necessary. Examples of apparatus in which the present systems and methods may be implemented are described in U.S. Pat. Nos. 5,993,398 and 6,245,027 and U.S. Publication No. 2011/0181285, which are incorporated by reference as if fully set forth herein.

The flow chart of FIG. 2B shows an example of functionality that may be implemented in the apparatus 1010 of FIG. 7. If embodied in software, each block shown in FIG. 2B may represent a module, segment, or portion of code that comprises program instructions to implement the specified logical function(s). The program instructions may be embodied in the form of source code that comprises machine code that comprises numerical instructions recognizable by a suitable execution system such as the processing device 202 (FIG. 7) in a computer system or other system. The machine code may be converted from the source code, etc. If embodied in hardware, each block may represent a circuit or a number of interconnected circuits to implement the specified logical function(s).

Although the flowchart of FIG. 2B shows a specific order of execution, it is understood that the order of execution may differ from that which is depicted. For example, the order of execution of two or more blocks may be scrambled relative to the order shown. Also, two or more blocks shown in succession in FIG. 2B may be executed concurrently or with partial concurrence. Further, in some embodiments, one or more of the blocks shown in FIG. 2B may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein that comprises software or code can be embodied in any non-transitory computer-readable medium for use by or in connection with an instruction execution system such as, for example, a processing device 202 in a computer system or other system. In this sense, each may comprise, for example, statements including instructions and declarations that can be fetched from the computer-readable medium and executed by the instruction execution system.

EXAMPLES

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for.

Example 1

In this example an embodiment of a present 2D golden angle radial ASL imaging method is utilized to label blood and continuously image the blood after labeling, allowing both angiographic and perfusion images to be reconstructed from the same raw data set. In this example we demonstrate one method for choosing the azimuthal angles of the acquired radial spokes across multiple ASL preparations, but many other options are possible.

Figure 8:
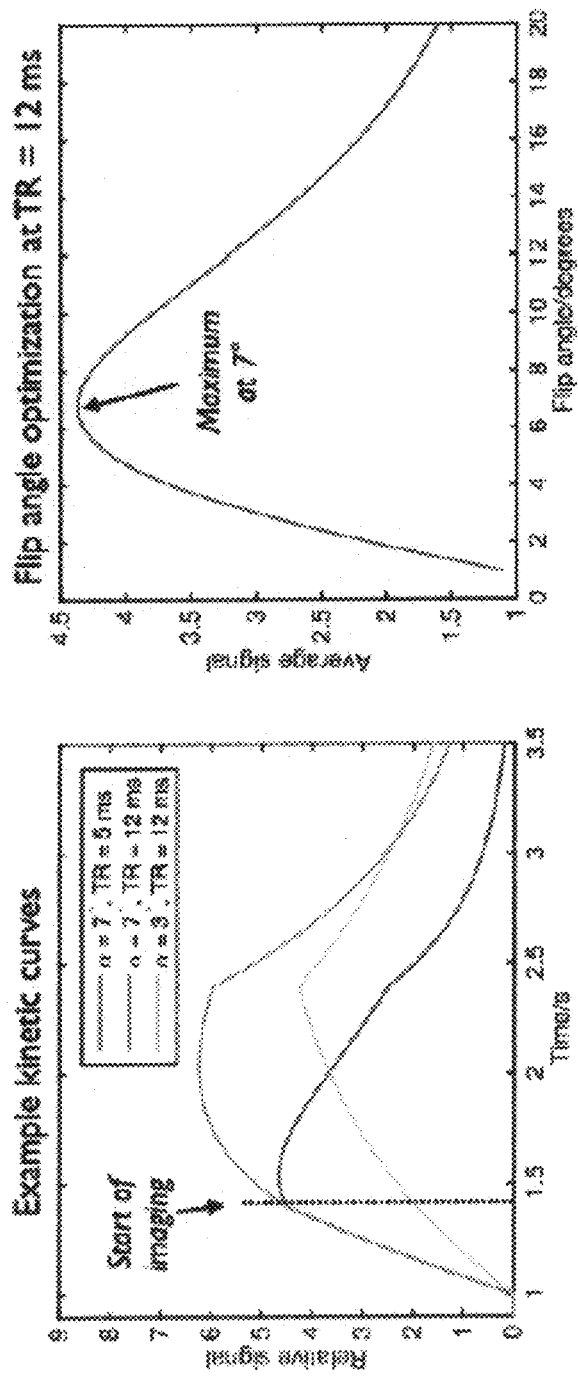
FIG. 8 illustrates examples of perfusion signal simulations with different imaging parameters: shorter pulse repetition times (TRs) and higher flip angles (α) can result in greater ASL signal attenuation (left). For the particular parameters used in this example (including a pseudo-continuous ASL labeling scheme of duration 1.4 s and an SPGR imaging method with TR=12 ms), the optimum flip angle in the example, as judged by the average perfusion signal over the imaging period, is 7° (right).

In this scheme, the azimuthal angle of the $i^{th}$ radial spoke after the $n^{th}$ PCASL preparation can be:

$$\phi_{i,n} = \left(n\frac{t_{max}}{TR} + i\right)\phi_G \text{ where } \phi_G = 111.2° \quad (1)$$

where $t_{max}$ is the maximum temporal resolution desired for reconstruction. This results in relatively even coverage of k-space when combining data within an arbitrary temporal window across multiple PCASL preparations, thereby allowing reconstruction of angiographic images at high temporal resolution and perfusion images at lower temporal resolution from the same raw data set. One skilled in the art will recognize, however, that other azimuthal angle increments can be used which may be linearly incremented by a different amount, non-linearly incremented or (pseudo)-randomly incremented. Acquisition of PCASL control data can be interleaved with label data to minimize subtraction artefacts from subject motion or scanner drift, although control data can also be acquired separately if desired. One skilled in the art will recognize, however that other azimuthal angles can be used. Numerical simulations of the ASL signal [30], accounting for attenuation due to the imaging pulses [31, 32], can be used to optimize the TR and flip angle. As illustrated in FIG. 8, shorter TRs and higher flip angles can result in greater ASL signal attenuation (left). Using TR=12 ms, which can result in reasonable under sampling factors, the optimum flip angle in the example, as judged by the average perfusion signal over the imaging period, is 7° (right).

Four healthy volunteers were scanned under a technical development protocol agreed by local ethics and institutional committees on a 3T Siemens Verio scanner using a 32-channel head coil. CAPRIA data were acquired in four 10 mm slices sequentially, each taking 2.5 min. Imaging parameters were: labeling duration 1.4 s, imaging time 2 s, matrix 192, TR/TE 12/6 ms, flip angle 7°, bandwidth 102 Hz/Pixel. While we used these specific parameters for this Example, other parameter values can be used, such as a labeling duration of 10 ms to 10,000 ms, an imaging time of 10 ms to 10,000 ms, TR from 1 ms to 1000 ms, TE from 0 to 500 ms, matrix of 5 to 1000, a flip angle of 0.01 to 180 degrees, and a bandwidth of 1 to 10,000 Hz/Pixel.

For this example, angiographic/perfusion images were reconstructed at 108/252 ms temporal resolution, respectively, using a regridding algorithm [33] and adaptive coil combination [34]. Perfusion images were post-hoc smoothed to boost SNR and match typical ASL in-plane resolution (3.4 mm). To give the appearance of inflowing blood in the angiograms, "inflow subtraction" was also performed [35, 36]. Simple outflow timing metrics [37] were calculated from angiographic images. Perfusion data were fitted to the ASL kinetic model [30] including a macrovascular component[38], with $T_1$ modified to account for the imaging pulses [31].

Figure 9:
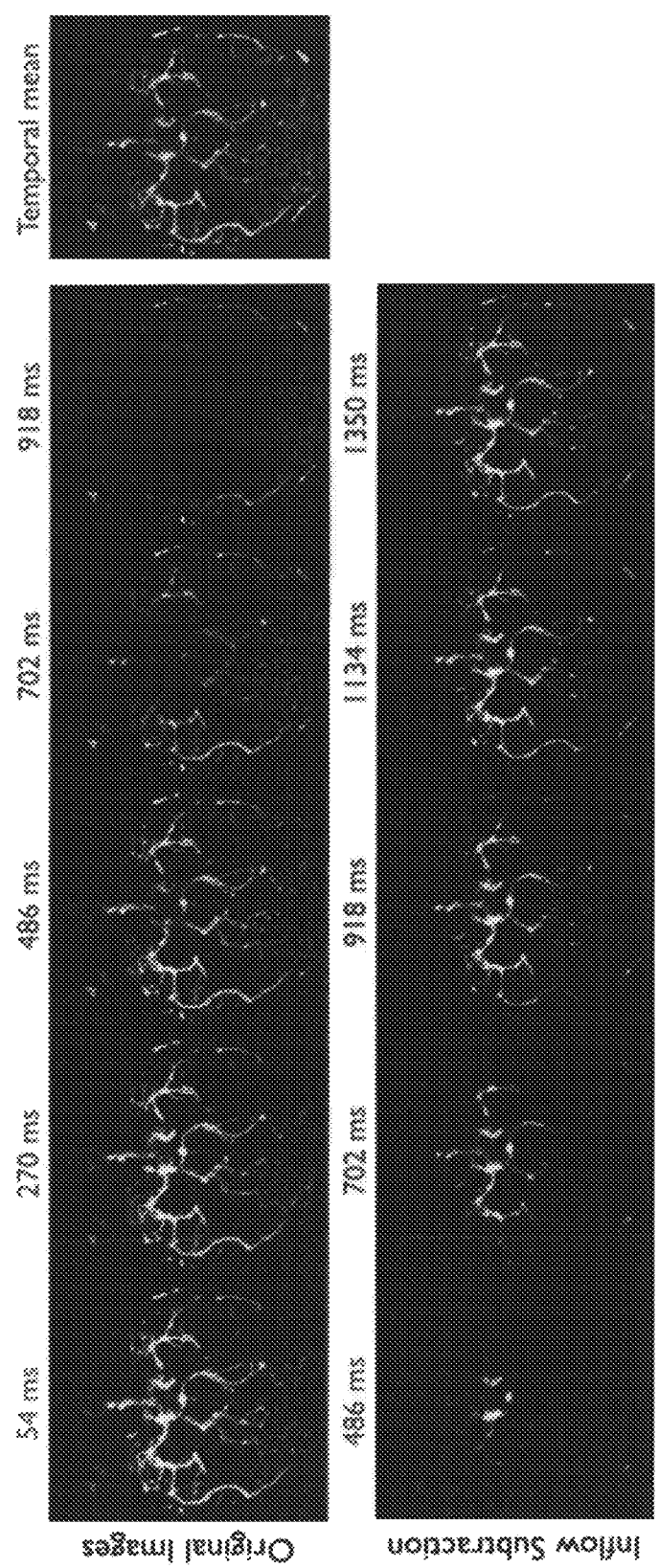
FIG. 9 shows selected frames from a 2D dynamic angiogram according to the present disclosure of one subject reconstructed at 108 ms temporal resolution (undersampling factor 1.6) after maximum intensity projection through four acquired slices. Images are shown with and without inflow subtraction along with the temporal mean (average of all frames). Times displayed are relative to the start of imaging.
Figure 10:
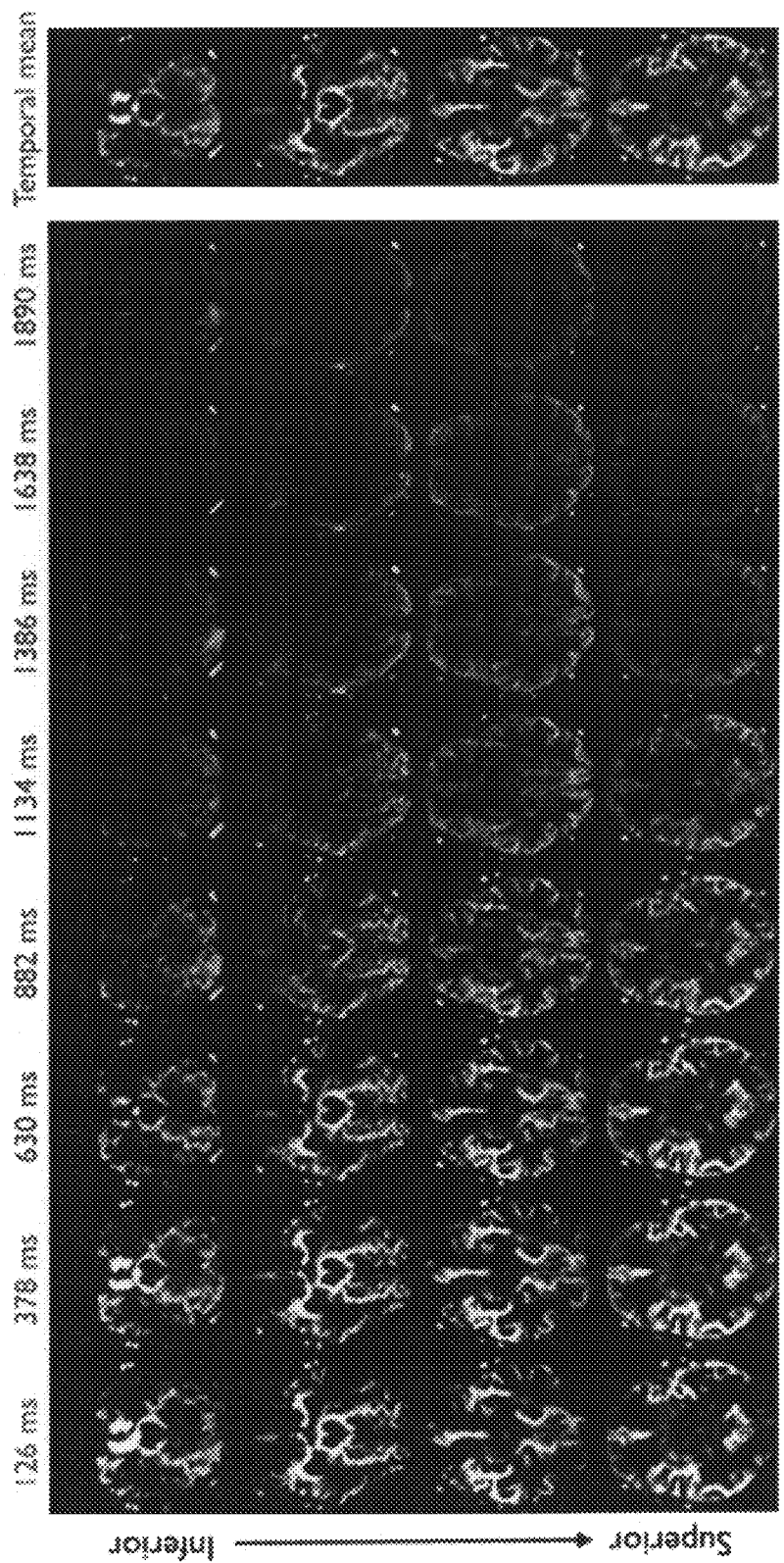
FIG. 10 shows examples of perfusion images according to the present disclosure reconstructed using the same raw data as FIG. 7, but with broader temporal resolution (252 ms, undersampling factor 0.7) and post-hoc spatial smoothing using a Gaussian kernel with standard deviation=1.75 mm. The temporal mean image is also shown. Times displayed are the post-labeling delays.
Figures 11A, 11B:
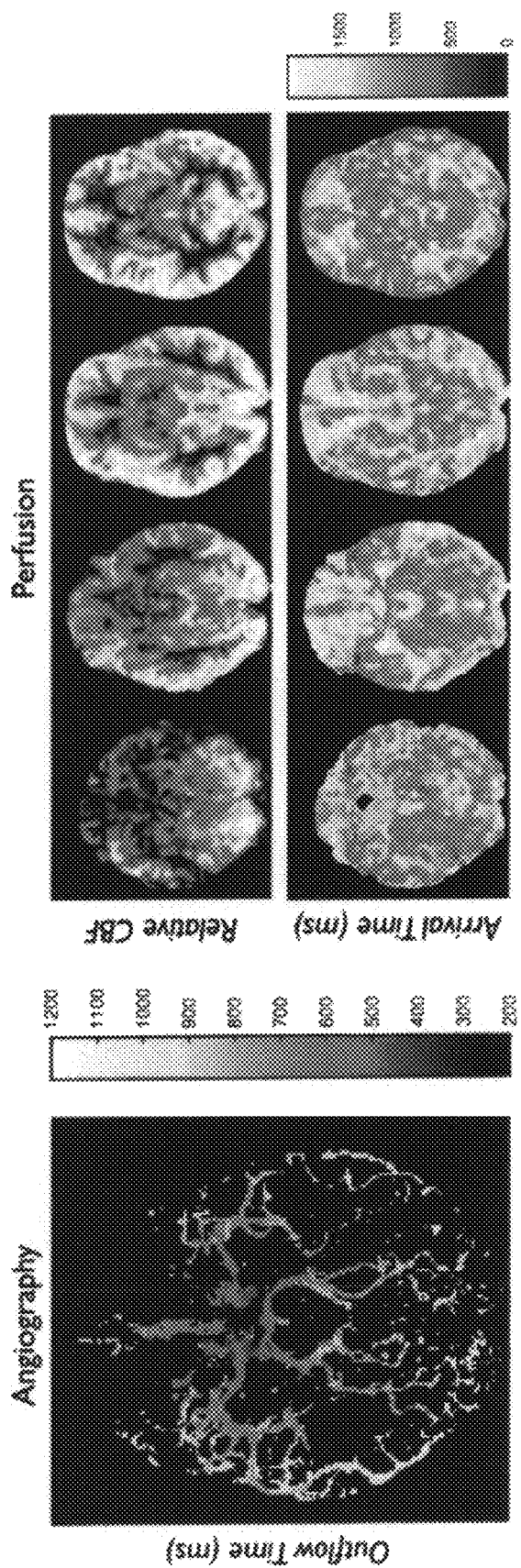
FIGS. 11A and 11B are an example of parameter maps of angiography and perfusion, respectively, according to the present disclosure. The angiographic outflow time roughly equates to the time of arrival of blood in the large arteries in the example, whereas the perfusion arrival time shows the arrival of blood at the tissue. Note that blood can have delayed arrival in distal vessels, watershed regions, and white matter.

The CAPRIA sequence is, thus, capable of simultaneously generating dynamic angiograms and perfusion images, as demonstrated in FIGS. 9 and 10. The expected patterns of vascular filling and tissue perfusion were observed in all subjects, in both the reconstructed images and the derived parameter maps (FIGS. 11A and 11B). The angiographic outflow time roughly equates to the time of arrival of blood in the large arteries in the example, whereas the perfusion arrival time shows the arrival of blood at the tissue. Note that blood can have delayed arrival in distal vessels, watershed regions, and white matter.

Example 2

In this example, four healthy volunteers were scanned under an agreed technical development protocol on a 3T Siemens Verio scanner using a 32-channel head coil. 4D CAPRIA data were acquired in 10 min (labeling duration 1.4 s, readout duration 2 s, matrix 160, 1.1 mm isotropic voxels, TR/TE 9/3.4 ms, flip angle 6° (CFA) or 2-9° (VFA), bandwidth 99 Hz/Pixel, readout partial Fourier 79%). Angiographic/perfusion images were reconstructed at 216/323 ms temporal resolution, respectively, using a regridding algorithm [33]. Perfusion image SNR was boosted via spatial smoothing to match typical ASL resolution (3.4 mm isotropic). Effective angiographic and perfusion undersampling factors were 19 and 2, respectively.

Example 4D CFA CAPRIA data are shown in FIG. 13. Good visualization of the proximal and distal arterial branches is achieved. Note that due to the long labeling duration the first angiographic image shows much of the arterial tree filled with labeled blood, with subsequent frames showing the filling of distal vessels and the passage of blood into the tissue. Perfusion images reconstructed from the same raw data set show the expected patterns of blood flow into the tissue, although the signal is weak at later time points.

Figure 14:
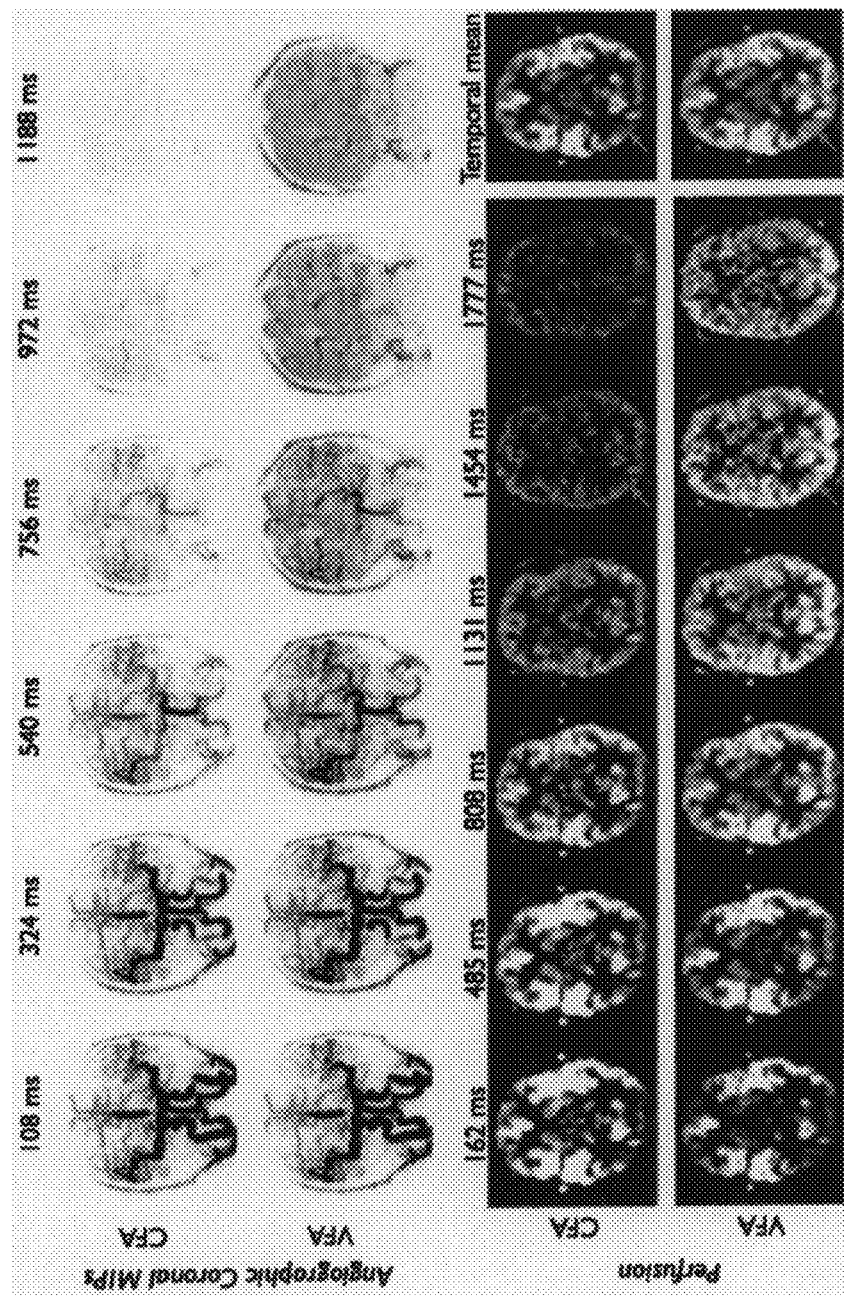
FIG. 14 depicts a comparison of CFA and VFA approaches.
Figure 15:
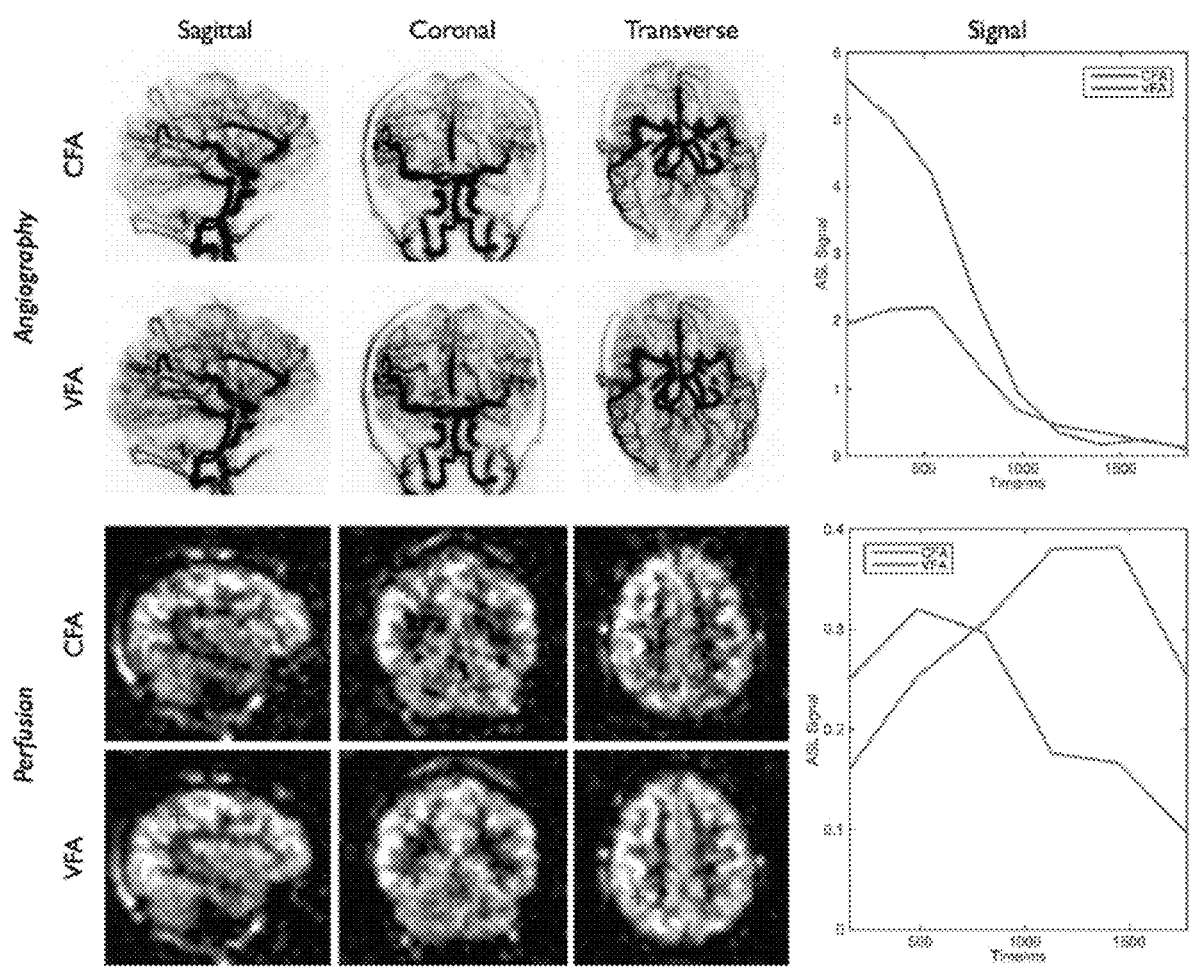
FIG. 15 depicts examples of measured signal timecourses for both CFA and VFA approaches.

A VFA scheme varying quadratically between 2° and 9° was found to give a considerable boost to the perfusion signal in simulations (FIGS. 6A-6C): for blood with an arterial transit time of 1.5 s the VFA signal is 82%/133% larger than the CFA signal at postlabeling delays of 1.5 s/2 s, respectively. Comparison of CFA and VFA schemes in the same subject (FIG. 14) reveal very little difference in angiographic image quality at early time points, despite the lower initial flip angle used with VFA, due to the high intrinsic SNR of this technique. Improved perfusion signal strength at later time points is also observed with VFA due to the reduced signal attenuation as the labeled blood accumulates in the tissue, as well as the direct impact of using larger flip angles at later time points. The observed signal timecourses were found to follow the trends expected from simulations (FIG. 15).

Thus, 4D CAPRIA allows the complete assessment of blood flow into the brain within a single scan, with a VFA approach yielding considerable improvements to perfusion image quality without adversely affecting the reconstructed angiograms. Reduction of noise-like radial undersampling artefacts using compressed sensing [29] can help improve image quality and/or reduce scan time.

The combined angiography and perfusion using radial imaging and arterial spin labeling (CAPRIA) sequence presented herein is, thus, well suited to this application, since dynamic angiograms require high spatial and temporal resolution, but are sparse and relatively high SNR, so undersampling can be tolerated. The converse is true of perfusion imaging, but lower spatial and temporal resolutions are required, so more data can be used to reconstruct each image and the denser sampling near the center of k-space improves the reconstruction. One additional benefit of this readout scheme is the absence of distortion and dropout artefacts that are often observed in conventional ASL perfusion imaging using readouts such as echo-planar imaging.

Acquisition of angiographic and perfusion images after ASL labeling has previously been shown using two separate dedicated readouts combined with a time-encoded preparation [39]. This can allow separate optimization of the two readout modules, but unlike CAPRIA, the timing of the resulting images must be decided in advance, so adaptation to the hemodynamics of each subject is not possible retrospectively.

Ratios, concentrations, amounts, and other numerical data may be expressed in a range format. It is to be understood that such a range format is used for convenience and brevity, and should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figure of the numerical value. In addition, the phrase "about 'x' to 'y'" includes "about 'x' to about 'y'".

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

REFERENCES 1. http://www.strokeassociation.org/STROKEORG/AboutStroke/Impact-of-Stroke-Stroke-statistics_UCM_310728_Article.jsp#.Vxd3SWO_1hw 2. Liebeskind D S. Imaging the future of stroke: I. Ischemia. *Ann Neurol* 2009; 66: 574-90.

3. Agarwal R, Brunelli S M, Williams K, et al. Gadolinium-based contrast agents and nephrogenic systemic fibrosis: a systematic review and meta-analysis. *Nephrol Dial Transplant* 2009; 24: 856-863.

4. Detre J A, Leigh J S, Williams D S, et al. Perfusion imaging. *Magn Reson Med* 1992; 23: 37-45.

5. Williams D S, Detre J A, Leigh J S, et al. Magnetic resonance imaging of perfusion using spin inversion of arterial water. *Proc Natl Acad Sci USA* 1992; 89: 212-216.

6. van Osch M J, Hendrikse J, Golay X, et al. Non-invasive visualization of collateral blood flow patterns of the circle of Willis by dynamic MR angiography. *Med Image Anal* 2006; 10: 59-70.

7. Okell T W, Chappell M A, Woolrich M W, et al. Vessel-encoded dynamic magnetic resonance angiography using arterial spin labeling. *Magn Reson Med* 2010; 64: 698-706.

8. Robson P M, Dai W, Shankaranarayanan A, et al. Time-resolved vessel-selective digital subtraction MR angiography of the cerebral vasculature with arterial spin labeling. *Radiology* 2010; 257: 507-515.

9. Bi X, Weale P, Schmitt P, et al. Non-contrast-enhanced four-dimensional (4D) intracranial MR angiography: a feasibility study. *Magn Reson Med* 2010; 63: 835-41.

10. Wu H, Block W F, Turski P A, et al. Noncontrast-enhanced three-dimensional (3D) intracranial MR angiography using pseudocontinuous arterial spin labeling and accelerated 3D radial acquisition. *Magn Reson Med* 2013; 69: 708-15.

11. Detre J A, Leigh J S, Williams D S, Koretsky A P. Perfusion imaging. Magn Reson Med 1992; 23:37-45.

12. Williams D S, Detre J A, Leigh J S, Koretsky A P. Magnetic resonance imaging of perfusion using spin inversion of arterial water. Proc Natl Acad Sci USA 1992; 89:212-216.

13. Alsop D C, Detre J A, Golay X, Gunther M, Hendrikse J, Hernandez-Garcia L, Lu H, Macintosh B J, Parkes L M, Smits M, van Osch M J P, Wang D J J, Wong E C, Zaharchuk G. Recommended implementation of arterial spin-labeled perfusion MRI for clinical applications: A consensus of the ISMRM perfusion study group and the European consortium for ASL in dementia. Magn Reson Med 2015; 73:102-16.

14. Dixon W T, Du L N, Faul D D, Gado M, Rossnick S. Projection angiograms of blood labeled by adiabatic fast passage. Magn Reson Med 1986; 3:454-462.

15. Nishimura D G, Macovski A, Pauly J M, Conolly S M. MR angiography by selective inversion recovery. Magn Reson Med 1987; 4:193-202.

16. Liebeskind D S. Collateral circulation. *Stroke* 2003; 34: 2279-84.

17. Winkelmann S, Schaeffter T, Koehler T, Eggers H, Doessel O. An optimal radial profile order based on the Golden Ratio for time-resolved MRI. IEEE Trans Med Imaging 2007; 26:68-76.

18. van der Meulen P, Groen J P, and Cuppen J J M. Very fast MR imaging by field echoes and small angle excitation. *Magnetic Resonance Imaging* 1985; 3: 297-299.

19. Scheffler K and Lehnhardt S. Principles and applications of balanced SSFP techniques. *Eur Radiol* 2003; 13: 2409-18.

20. Schmitt P, Speier P, Bi X, et al. Non-contrast-enhanced 4D intracranial MR angiography: Optimizations using a variable flip angle approach. In *Proceedings 18th Scientific Meeting, ISMRM*, Stockholm, Sweden, 2010; p. 402.

21. Barger A V, Block W F, Toropov Y, et al. Time-resolved contrast-enhanced imaging with isotropic resolution and broad coverage using an undersampled 3D projection trajectory. *Magn Reson Med* 2002; 48: 297-305.

22. Winkelmann S, Schaeffter T, Koehler T, et al. An optimal radial profile order based on the Golden Ratio for time-resolved MRI. *IEEE Trans Med Imaging* 2007; 26: 68-76.

23. Chan R W, Ramsay E A, Cunningham C H, et al. Temporal stability of adaptive 3D radial MRI using multidimensional golden means. *Magnetic Resonance in Medicine* 2009; 61: 354-363.

24. Buxton R B, Frank L R, Wong E C, et al. A general kinetic model for quantitative perfusion imaging with arterial spin labeling. *Magn Reson Med* 1998; 40: 383-396.

25. Wong E C. Vessel-encoded arterial spin-labeling using pseudocontinuous tagging. *Magn Reson Med* 2007; 58: 1086-1091.

26. Okell T W, Garcia M, Chappell M A, et al. Assessment of Arterial Supply to Arteriovenous Malformations with Vessel-Encoded Arterial Spin Labeling Dynamic Angiography. In *Proceedings 21st Scientific Meeting, ISMRM,* Salt Lake City, USA, 2013; p. 1128.

27. White N, Roddey C, Shankaranarayanan A, et al. PROMO: Real-time prospective motion correction in MRI using image-based tracking. *Magn Reson Med* 2010; 63: 91-105.

28. Lee J, Santos J M, Conolly S M, et al. Respiration-induced B0 field fluctuation compensation in balanced SSFP: real-time approach for transition-band SSFP fMRI. *Magn Reson Med* 2006; 55: 1197-201.

29. Lustig M, Donoho D, and Pauly J M. Sparse MRI: The application of compressed sensing for rapid MR imaging. *Magn Reson Med* 2007; 58: 1182-95.

30. Buxton R B, Frank L R, Wong E C, Siewert B, Warach S, Edelman R R. A general kinetic model for quantitative perfusion imaging with arterial spin labeling. Magn Reson Med 1998; 40:383-396.

31. Gunther M, Bock M, Schad L R. Arterial spin labeling in combination with a Look-Locker sampling strategy: inflow turbosampling EPI-FAIR (ITS-FAIR). Magn Reson Med 2001; 46:974-84.

32. Okell T W, Chappell M A, Schulz U G, Jezzard P. A kinetic model for vessel-encoded dynamic angiography with arterial spin labeling. Magn Reson Med 2012; 68:969-979.

33. Fessler J. Image Reconstruction Toolbox. http://web.eecs.umich.edu/~fessler/irt. October 2015.

34. Walsh D O, Gmitro A F, Marcellin M W. Adaptive reconstruction of phased array MR imagery. Magn Reson Med 2000; 43:682-90.

35. Okell T W, Schmitt P, Bi X, Chappell M A, Tijssen R H, Miller K L, Jezzard P. 4D Vessel-Encoded Arterial Spin Labeling Angiography. In Proceedings 19th Scientific Meeting, ISMRM, Montreal, Canada, 2011. p 4034.

36. Kopeinigg D, Bammer R. Time-resolved angiography using inflow subtraction (TRAILS). Magn Reson Med 2014; 72:669-678.

37. Okell T W, Chappell M A, Woolrich M W, Gunther M, Feinberg D A, Jezzard P. Vessel-encoded dynamic magnetic resonance angiography using arterial spin labeling. Magn Reson Med 2010; 64:698-706.

38. Chappell M A, Macintosh B J, Donahue M J, Gunther M, Jezzard P, Woolrich M W. Separation of macrovascular signal in multiinversion time arterial spin labeling MRI. Magn Reson Med 2010; 63:1357-1365.

39. Suzuki Y, Teeuwisse W M, Schmid S, Koken P, Cauteren M V, Helle M, van Osch M J. Simultaneous acquisition of perfusion maps and 4D MR angiography by means of arterial spin labeling MRI. In Proceedings 22nd Scientific Meeting, ISMRM, Milan, Italy, 2014. p 720.

40. H. Wu, W. F. Block, P. A. Turski, C. A. Mistretta, D. J. Rusinak, Y. Wu, and K. M. Johnson, "Non-contrast dynamic 3d intracranial mr angiography using pseudo-continuous arterial spin labeling (pcasl) and accelerated 3d radial acquisition," J Magn Reson Imaging, vol. 39, pp. 1320-6, May 2014.

41. T. W. Okell, P. Schmitt, X. Bi, M. A. Chappell, R. H. Tijssen, F. Sheerin, K. L. Miller, and P. Jezzard, "Optimization of 4d vessel-selective arterial spin labeling angiography using balanced steady-state free precession and vessel-encoding." In Press, DOI: 10.1002/nbm.3515, 2016.

42. D. Kopeinigg and R. Bammer, "Time-resolved angiography using inflow subtraction (trails)," Magn Reson Med, vol. 72, pp. 669-678, September 2014.

43. Okell T W. Combined Angiography and Perfusion using Radial Imaging and Arterial Spin Labeling. In Proceedings 24th Scientific Meeting, ISMRM, Singapore, 2016. p 1001.

Therefore, the following is claimed:

1. A computer implemented method for combined angiography and perfusion imaging using radial imaging, comprising:
   labeling blood for dynamic imaging with arterial spin labeling and without use of a contrast agent;
   acquiring a data set from the labeled blood using radial imaging and a continuous readout scheme;
   reconstructing one or more angiography images from the data set, wherein the one or more reconstructed angiography images are reconstructed with a spatial and temporal resolution for angiography; and
   separately reconstructing one or more perfusion images from the data set, wherein the one or more reconstructed perfusion images are reconstructed with a spatial and temporal resolution for perfusion imaging,
   wherein the step of separately reconstructing one or more perfusion images includes separately reconstructing the one or more perfusion images from the same data set from which the one or more angiography images are reconstructed.

2. The method of claim 1, wherein the arterial spin labeling (ASL) is pseudo-continuous ASL, time-encoded ASL, pulsed ASL, or vessel-selective ASL.

3. The method of claim 1, wherein the radial imaging includes incrementing changing an azimuthal angle wherein the azimuthal angle is non-linearly incremented.

4. The method of claim 1, wherein the angiography temporal resolution is higher than the perfusion temporal resolution.

5. The method of claim 1, wherein the radial imaging includes taking full radial samples in a plane.

6. The method of claim 1, wherein the radial imaging includes acquiring non-cartesian radial samples within a sphere of k-space.

7. The method of claim 1, wherein the radial imaging is performed to allow reconstructing the one or more images at variable temporal resolution.

8. The method of claim 7, wherein the radial imaging is performed to allow reconstructing the one or more images at variable spatial resolution.

9. The method of claim 1, further comprising processing the one or more reconstructed angiography images with inflow subtraction.

10. The method of claim 1, further comprising processing the one or more reconstructed angiography images or the one or more reconstructed perfusion images with post-hoc spatial smoothing, or both.

11. The method of claim 1, wherein the acquired data set includes data from a readout module;
   the one or more angiography images are reconstructed from data from the readout module; and
   the one or more perfusion images are reconstructed from data from the readout module from which the one or more angiography images are also reconstructed.

12. A system comprising:
   at least one computing device;
   at least one application executable in the at least one computing device, the at least one application comprising logic that:
   A. labels blood for dynamic imaging with arterial spin labeling and without use of a contrast agent;
   B. acquires a data set from the labeled blood set using radial imaging and a continuous readout scheme;
   C. reconstructs one or more angiography images from the data set, wherein the one or more reconstructed angiography images are reconstructed with a spatial and temporal resolution for angiography; and D. separately reconstructs one or more perfusion images from the data set, wherein the one or more reconstructed perfusion images are reconstructed with a spatial and temporal resolution for perfusion imaging, wherein the step of separately reconstructing one or more perfusion images includes separately reconstructing the one or more perfusion images from the same data set from which the one or more angiography images are reconstructed.

13. The system of claim 12, wherein arterial spin labeling (ASL) is pseudo-continuous ASL, time-encoded ASL, pulsed ASL, or vessel-selective ASL.

14. The system of claim 12, wherein the radial imaging includes incrementing an azimuthal angle wherein the azimuthal angle is non-linearly incremented.

15. The system of claim 12, wherein the angiography temporal resolution is higher than the perfusion temporal resolution.

16. The system of claim 12, wherein the radial imaging includes taking full radial samples in a plane.

17. The system of claim 12, wherein the radial imaging includes acquiring non-cartesian radial samples within a sphere of k-space.

18. The system of claim 12, wherein the radial imaging is performed to allow reconstructing the one or more images at variable temporal resolution.

19. The system of claim 18, wherein the radial imaging is performed to allow reconstructing the one or more images at variable spatial resolution.

20. The system of claim 12, wherein the logic further comprises logic that:

E. processes the one or more reconstructed angiography images with inflow subtraction.

21. The system of claim 20, wherein the logic further comprises logic that:

F. processes the reconstructed angiography images with post-hoc spatial smoothing.

22. The system of claim 21, wherein the logic further comprises logic that:

G. processes the reconstructed perfusion images with post-hoc spatial smoothing.

23. The system of claim 12, wherein the radial imaging is a Golden Ratio radial readout scheme providing the continuous readout scheme to continuously image the labeled blood through large arteries and into the tissue of a subject.

24. The system of claim 12, wherein the acquired data set includes data from a readout module;

the one or more angiography images are reconstructed from data from the readout module; and the one or more perfusion images are reconstructed from data from the readout module from which the one or more angiography images are also reconstructed.

25. A computer implemented method for combined angiography and perfusion imaging using radial imaging, comprising:

labeling blood for dynamic imaging with arterial spin labeling and without use of a contrast agent;

acquiring a data set from the labeled blood using radial imaging and a continuous readout scheme;

reconstructing one or more angiography images from the data set, wherein the one or more reconstructed angiography images are reconstructed with a spatial and temporal resolution for angiography;

separately reconstructing one or more perfusion images from the data set, wherein the one or more reconstructed perfusion images are reconstructed with a spatial and temporal resolution for perfusion imaging; and wherein the radial imaging is a Golden Ratio radial readout scheme providing the continuous readout scheme to continuously image the labeled blood through large arteries and into the tissue of a subject.

* * * * *